US012807664B2

(12) United States Patent
Karin et al.

(10) Patent No.: US 12,807,664 B2
(45) Date of Patent: Nov. 24, 2026

(54) MODIFIED CXCL10 FOR IMMUNOTHERAPY OF CANCER DISEASES

(71) Applicant: TECHNION RESEARCH & DEVELOPMENT FOUNDATION LIMITED, Haifa (IL)

(72) Inventors: Nathan Karin, Haifa (IL); Ghada Jarrous, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 938 days.

(21) Appl. No.: 18/080,149

(22) Filed: Dec. 13, 2022

(65) Prior Publication Data

US 2023/0212247 A1 Jul. 6, 2023

Related U.S. Application Data

(63) Continuation of application No. PCT/IL2021/050750, filed on Jun. 21, 2021.

(60) Provisional application No. 63/150,622, filed on Feb. 18, 2021, provisional application No. 63/041,936, filed on Jun. 21, 2020.

(51) Int. Cl.
*C07K 14/52* (2006.01)
*A61K 47/68* (2017.01)
*A61P 35/00* (2006.01)

(52) U.S. Cl.
CPC ........ *C07K 14/521* (2013.01); *A61K 47/6813* (2017.08); *A61P 35/00* (2018.01); *C07K 2319/30* (2013.01)

(58) Field of Classification Search
CPC .............. C07K 14/521; C07K 2319/30; A61K 47/6813; A61K 38/00; A61P 35/00
See application file for complete search history.

(56) References Cited

U.S. PATENT DOCUMENTS 5,595,756 A * 1/1997 Bally .................. A61K 9/1272 264/4.1
6,777,196 B2 8/2004 Klein et al.
7,083,784 B2 8/2006 Dall'Acqua et al.
8,541,564 B2 9/2013 Lillard, Jr.
2022/0017585 A1* 1/2022 Yamamoto ........... C07K 14/521

FOREIGN PATENT DOCUMENTS

WO 96/32478 A1 10/1996
WO 97/34631 A1 9/1997
WO WO-2020116498 A1 * 6/2020 .............. C12P 21/02

OTHER PUBLICATIONS

Heppner et al, Cancer Metastasis Review 2:5-23; 1983 (Year: 1983).*
Lazar et al., Mol. Cell. Biol., 8:1247-1252, 1988 (Year: 1988).*
Burgess et al., J. Cell Biol. 111:2129-2138, 1990 (Year: 1990).*
Jain RK, Scientific American, Jul. 1994,58-65 (Year: 1994).*
Brown et al., J Immunol. May 1996;156(9):3285-9 (Year: 1996).*
Gura T, Science, 1997, 278(5340): 1041-1042 (Year: 1997).*
Greenspan et al. 1999; Nature Biotechnology, 17:936-937 (Year: 1999).*
Sporn et al., Chemoprevention of Cancer, Carcinogenesis, vol. 21 (2000), 525-530 (Year: 2000).*
Auerbach et al., Cancer and Metastasis Reviews, 2000, 19: 167-172 (Year: 2000).*
Skolnick et al., Trends Biotechnol. Jan. 2000;18(1):34-9 (Year: 2000).*
Bork, Genome Research, 2000,10:398-400 (Year: 2000).*
Vajdos et al., J Mol Biol. Jul. 5, 2002;320(2):415-28 (Year: 2002).*
Hait, Nature Reviews/Drug Discovery, 2010, 9, pp. 253-254 (Year: 2010).*
Liu et al, Oncology Letters 2: 583-589, 2011 (Year: 2011).*
Gravanis et al., Chin Clin Oncol, 2014, 3, pp. 1-5 (Year: 2014).*
Miosge, Proc Natl Acad Sci U S A. Sep. 15, 2015;112(37):E5189-98 (Year: 2015).*
Beans, PNAS 2018; 115(50): 12539-12543 (Year: 2018).*
Kulmanov et al, Bioinformatics, 34(4), 2018, 660-668 (Year: 2018).*
Baldo, Brian A. "Chimeric fusion proteins used for therapy: indications, mechanisms, and safety." Drug safety 38.5 (2015): 455-479. doi: 10.1007/s40264-015-0285-9. PMID: 25832756.
Zohar et al (2004) CXCL 11-dependent induction of FOXP3-negative regulatory T cells suppresses autoimmune encephalomyelitis. Journal Clin. Invest., 124(5):2009-2022. https://doi.org/10.1172/JCI71951.
Loos et al (2008) Citrullination of CXCL10 and CXCL11 by peptidylarginine deiminase: a naturally occurring posttranslational modification of chemokines and new dimension of immunoregulation, Blood, 112(7):2648-2656. doi: 10.1182/blood-2008-04-149039. Epub Jul. 21, 2008. PMID: 18645041.
Shen et al (2005) Engineered recombinant single-chain fragment variable antibody for immunosensors, Anal Chem, 77(21):6834-6842. doi:10.1021/ac0507690.
Bronger et al (2019) Proteolytic chemokine cleavage as a regulator of lymphocytic infiltration in solid tumors, Cancer and Metastasis Reviews, 38:417-430, https://doi.org/10.1007/s10555-019-09807-3.
Kim et al (2014) Effective Therapeutic Approach for Head and Neck Cancer by an Engineered Minibody Targeting the EGFR Receptor, PloS one 9, e113442. doi:10.1371/journal.pone.0113442.
Chow et al (2019) Intratumoral Activity of the CXCR3 Chemokine System is Required for the Efficacy of Anti-PD-1 Therapy, Immunity 50:1498-1512 e5. https://doi.org/10.1016/j.immuni.2019.04.010.

(Continued)

*Primary Examiner* — Vanessa L. Ford
*Assistant Examiner* — Danaya L Middleton
(74) *Attorney, Agent, or Firm* — The Roy Gross Law Firm, LLC; Roy D. Gross

(57) ABSTRACT

The invention provides a modified CXCL10 polypeptide, comprising an insertion of an additional amino acid at the N-terminus of a corresponding wild type CXCL10, pharmaceutical composition comprising the same and method for using thereof for treating cancer.

6 Claims, 17 Drawing Sheets

Specification includes a Sequence Listing.

(56) References Cited

OTHER PUBLICATIONS

Arenberg et al (2001) Improved survival in tumor-bearing SCID mice treated with interferon-gamma-inducible protein 10 (IP.10/CXCL10), Cancer immunology immunotherapy C11 50:533-538. DOI: 10.1007/s00262-001-0231-9.

Barash et al (2014) Heparanase enhances myeloma progression via CXCL 10 down regulation, Leukemia, 28:2178-2187. doi:10.1038/leu.2014.121.

Peng et al (2015) Epigenetic silencing of TH1 type chemokines shapes tumor immunity and immunotherapy, Nature, 527:249-253. doi: 10.1038/nature15520.

Berreira da Silva et al (2015) Dipeptidylpeptidase 4 inhibition enhances lymphocyte trafficking, improving both naturally occuring tumor immunity and immunotherapy, Nature Immunology 16:850-858. doi: 10.1038/ni.3201.

Antonicelli et al (2011) CXCL10 reduces melanoma proliferation and invasiveness in vitro and in vivo, The British Journal of Dermatology 164:720-728. DOI 10.1111/j.1365-2133.2010.10176.x.

Vasquez and Soong (2006) CXCL10/Gamma Interferon-Inducible Protein 10-Mediated Protection against Leishmania amazonensis Infection in Mice, Infection and Immunity, pp. 6769-6777. doi:10.1128/IAI.01073-06.

Barsheshet et al (2017) CCR8+FOXp3+ Treg cells as master drivers of immune regulation, PNAS 114(23):6086-6091. www.pnas.org/cgi/doi/10.1073/pnas.1621280114.

Vanheule et al (2018) How post-translational modifications influence the biological activity of chemokines, Cytokine 109:29-51. https://doi.org/10.1016/j.cyto.2018.02.026.

PCT International Search Report for International Application No. PCT/IL2021/050750, mailed Sep. 9, 2021, 4pp.

PCT Written Opinion for International Application No. PCT/IL2021/050750, mailed Sep. 9, 2021, 8pp.

PCT International Preliminary Report on Patentability for International Application No. PCT/IL2021/050750, issued Dec. 13, 2022, 7pp.

Zettlitz, K.A., Chapter 34: Protein A/G Chromatography. In: Kontermann, R., Dubel, S. (Eds) Antibody Engineering. Springer Protocols Handbooks. Springer, Berlin, Heidelberg, vol. 1, pp. 531-535, 2010. https://doi.org/10.1007/978-3-642-01144-3_34.

Strohl, W., Fusion Proteins for Half-Life Extension of Biologics as a Strategy to Make Biobetters, BioDrugs, 29:215-239, 2015. doi: 10.1007/s40259-015-0133-6. PMID: 26177629; PMCID: PMC4562006.

* cited by examiner

***P<0.0014

***P<0.0014

```
Aligned_sequences: 2
# 1: HOMO SAPIENCE CXCL10_001
# 2: MUS MULUSCUM CXCL10_001
# Matrix: EBLOSUM62
# Gap_penalty: 10.0
# Extend_penalty: 0.5
#
# Length: 98
# Identity:      67/98 (68.4%)
# Similarity:    79/98 (80.6%)
# Gaps:           0/98 ( 0.0%)
# Score: 340.0
#=======================================            Arginine at position 5
                          Signal peptide
H.S CXCL10_001     1 MNQTAILICCLIFLTLSGIQGVPLSRTVRCTCISISNQPVNPRSLEKLEI     50
                     ||.:|.:|.|||.|.|||.||:||:|||||.||.|.:.||..|::.||||
M.M. CXCL10_001    1 MNPSAAVIFCLILLGLSGTQGIPLARTVRCNCIHIDDGPVRMRAIGKLEI     50

H.S CXCL10_00     51 IPASQFCPRVEIIATMKKKGEKRCLNPESKAIKNLLKAVSKERSKRSP     98
                     ||||..||||||||||||..|:||||||||.||||:||.|::||||:|
M.M.CXCL10_0      51 IPASLSCPRVEIIATMKKNDEQRCLNPESKTIKNLMKAFSQKRSKRAP     98
```

Figure 1D

MODIFIED CXCL10 FOR IMMUNOTHERAPY OF CANCER DISEASES

CROSS REFERENCE TO RELATED APPLICATIONS

This application is a Bypass continuation of PCT Patent Application No. PCT/IL2021/050750 having International filing date of Jun. 21, 2021, which claims the benefit of priority of U.S. Provisional Patent Application No. 63/041, 936, filed Jun. 21, 2020 and U.S. Provisional Patent Application No. 63/150,622, filed Feb. 18, 2021, the contents of which are all incorporated herein by reference in their entirety.

REFERENCE TO AN ELECTRONIC SEQUENCE LISTING

The contents of the electronic sequence listing (TECH_017_WOUS.xml; Size: 69,720 bytes; and Date of Creation: Jan. 25, 2023) is herein incorporated by reference in its entirety.

BACKGROUND OF THE INVENTION

While many chemokines that are produced by cancer cells, that also possess their receptors, clearly support tumor growth and suppress anti-cancer immune reactivity, the CXCR3 ligand CXC10 is thought to support tumor growth by eliciting an anti-cancer immune response. CXCL10 may also directly inhibit tumor growth. CXCR3 is a chemokine receptor with three ligands: CXCL9, CXCL10 and CXCL11. The different CXCR3 ligands may differ in their biological functions.

Several studies showed that CXCL10 produced by tumor or host cells can recruit CXCR3+ tumor-infiltrating CD4+ T cells, CD8+ T cells and NK cells that are associated with tumor suppression. A recent study showed that CXCL10 also affect the tissue distribution of CD8+ T cells in naïve mice. As for cancer, Zumwalt et al showed active secretion of CXCL10 and CCL5 from colorectal cancer microenvironments in human was associated with Granzyme B+CD8+ T-cell infiltration. It was shown that anti PD-1 efficacy is reduced in CXCR3KO mice, and suggested that the interaction between CXCL9, largely produced by CD103+ dendritic cells (DC) at the tumor site, and CXCR3 on CD8+ T cells enhances anti PD-1 efficacy (Chow et al, *Immunity* 2019, 50 1498-1512 e5).

Arenberg et al showed that intra-tumoral injection of CXCL10 limits non-small-cell lung cancer (NSCLC) in SCID mice by a direct effect on tumor growth (Arenberg, D. A., White, E. S., Burdick, M. D., Strom, S. R. & Strieter, R. M. Improved survival in tumor-bearing SCID mice treated with interferon-gamma-inducible protein 10 (IP-10/CXCL10). *Cancer immunology, immunotherapy: CII* 50, 533-538. (2001)). Further, it was shown that systemic administration of CXCL10 (CXCL10-Ig) limits cancer in immunocompetent mice (Barash, U., Zohar, Y., Wildbaum, G., Beider, K., Nagler, A., Karin, N., Ilan, N. & Vlodavsky, I. Heparanase enhances myeloma progression via CXCL10 downregulation. Leukemia 28, 2178-2187 (2014)).

Peng et al showed that treatment with epigenetic modulators that increase CXCL9/CXCL10 enhances effector T-cell tumor infiltration, and slows down tumor progression of ovarian cancer (Peng, D., Kryczek, I., Nagarsheth, N., Zhao, L., Wei, S., Wang, W., Sun, Y., Zhao, E., Vatan, L., Szeliga, W., Kotarski, J., Tarkowski, R., Dou, Y., Cho, K., Hensley-Alford, S., Munkarah, A., Liu, R. & Zou, W. Epigenetic silencing of TH1-type chemokines shapes tumour immunity and immunotherapy. *Nature* 527, 249-253 (2015)).

Barreiara da Silva et al showed that Dipeptidylpeptidase 4 inhibition enhances endogenous CXCL10 levels and suppresses B16/F10 melanoma growth (Barreira da Silva, R., Laird, M. E., Yatim, N., Fiette, L., Ingersoll, M. A. & Albert, M. L. Dipeptidylpeptidase 4 inhibition enhances lymphocyte trafficking, improving both naturally occurring tumor immunity and immunotherapy. *Nature immunology* 16, 850-858 (2015)).

The role of CXCL10 in limiting metastatic melanoma has yet to be examined.

Collectively, all these data clearly indicate for a role of CXCL10 in suppressing cancer development in humans. As for melanoma it has been shown that of many cytokines and chemokine that were tested only CXCL10 is significantly increased in melanoma patients with remission compared with patients with progression. The paper also shows that CXCL10 suppresses the in vitro proliferation of B16 melanoma line cells, and that over expression of CXCL10 (viral transfection) suppresses B16 melanoma (Antonicelli, F., Lorin, J., Kurdykowski, S., Gangloff, S. C., Le Naour, R., Sallenave, J. M., Hornebeck, W., Grange, F. & Bernard, P. CXCL10 reduces melanoma proliferation and invasiveness in vitro and in vivo. The British journal of dermatology 164, 720-728 (2011)).

The in vivo stability of chemokines, particularly CXCL10 is very limited (Vasquez & Soong, Infection and Immunity, December 2006, p. 6769-6777). It was shown that generation of stabilized chemokines as fusion proteins with Ig FC leads to prolong in vivo half-life (Barsheshet et al *PNAS* 2017). Yet it appears that the short half-life of CXCL10, even if being generated as fusion protein is relatively limited due to enzymatic inactivation, in particular citrullination by PAD (Loos et al, *Blood.* 2008 Oct. 1; 112 (7): 2648-56. doi: 10.1182/blood-2008-04-149039. Epub 2008 Jul. 21).

The in vivo activity of CXCL10, particularity at tumor sites, is regulated by two different enzymes that induce post translational modifications (PTM) (Barreira da Silva et al., 2015; Metzemaekers et al., 2017; Vanheule et al., 2018). This includes citrullination of the Arginine at position 5, by Peptidyl Arginine Deiminase 4 (PAD 4) resulting in activity loss (Metzemaekers et al., 2017; Vanheule et al., 2018), and cleavage of CXCL10 by Dipeptidyl peptidase 4 (DPP4, also known as CD26) that acts on the proline at position 3 thus induces cleavage of the 2 N-terminus amino acids, resulting in a none-functional CXCL10, that may also act as an antagonist chemokine to CXCL10 (Barreira da Silva et al., 2015; Metzemaekers et al., 2017; Vanheule et al., 2018), as the truncated protein may inhibit intact CXCL10 (Charles and Dustin, 2011).

Systemic targeting of DPP4 may thus be beneficial in inhibiting cancer development (Barreira da Silva et al., 2015), but may hold major side effects due to the critical role of this enzyme in regulating different biological functions, among them glucose metabolism (Leong, 2018).

There is a need to develop modified CXCL10 polypeptides that will be stable and efficient as anticancer drugs and further will be resistant to DPP4 cleavage.

SUMMARY OF THE INVENTION

According to some embodiments, there is provided an advantageous modified CXCL10 polypeptide, which includes one or more-point mutations and/or insertion compared to a wild-type (non-modified) CXCL10. According to some embodiments, the novel, non-naturally occurring, modified CXCL10 disclosed herein is advantageous, as it is stable, easy to produce, and exhibit a desired biological activity, as further detailed herein. Further provided are nucleic acids encoding for the modified CXCL10 polypeptide, methods for the preparation of the modified CXCL10, compositions comprising the same and uses thereof in treating various medical conditions, in particular, cancer.

In some embodiments, there is provided a modified CXCL10 polypeptide, comprising an insertion of one or more additional amino acid at the N-terminus of a corresponding wild type CXCL10 having an amino acid sequence as denoted by SEQ ID NO: 1.

In some embodiments, there is provided a modified CXCL10 polypeptide, comprising an insertion of an additional amino acid at the N-terminus of a corresponding wild type CXCL10. The additional amino acid may be any amino acid. In some embodiments, there is provided a modified CXCL10 polypeptide, comprising an insertion of an additional amino acid at the N-terminus of a corresponding wild type CXCL10 having an amino acid sequence as denoted by SEQ ID NO: 1. In some embodiments, the additional amino acid is glutamine, asparagine, pyroglutamate, glutamic acid or proline. In some embodiments, the additional amino acid is Phenylalanine, Leucine, Isoleucine, Valine, Tyrosine, Histidine, Lysine, aspartate, glutamate, Arginine or Glycine.

In some embodiments, the wild type CXCL10 is of human origin. In some embodiments, the modified CXCL10 polypeptide comprises an amino acid sequence as denoted, for example, by any one of SEQ ID NOs: 2-4.

In some embodiments, the modified CXCL10 polypeptide described herein is linked to an immunoglobulin (Ig) molecule or a fragment of an Ig molecule. The immunoglobulin is in some embodiments, IgG-Fc: hinge-ch2-ch3 denoted by SEQ ID No: 5. In some embodiments, the modified CXCL10 polypeptide described herein, is linked to an immunoglobulin (Ig) molecule or a fragment of an Ig molecule, further comprises a linker between the modified CXCL10 and the immunoglobulin molecule or the fragment thereof. In some embodiments, the immunoglobulin or the fragment thereof is of human origin. In some embodiments, the linker comprises a stretch of one or more Glycine amino acids (poly G) or a stretch of Glycine and Serine amino acids (poly GS), such as for example, one or more units of GGGGS (SEQ ID No: 7).

In some embodiments, the poly GS is GGGGSGGGGSGGGGS (SEQ ID No: 6).

In some embodiments, the modified CXCL10 polypeptide is capable of binding to CXCR3 receptor. In some embodiments, the modified CXCL10 polypeptide may induce (potentiate) the activity of CD8+ T cells by eliciting the levels of interferon gamma (IFN-g), tumor necrosis factor alpha (TNFa), Granzyme-B, perforin, and Interleukin 2 (IL-2).

In some embodiments, there is provided a fusion protein comprising CXCL10 polypeptide, which may be WT or mutated CXCL10, conjugated to an immunoglobulin molecule or a fragment of an Ig molecule. In some embodiments, the immunoglobulin or the fragment thereof is IgG-Fc: hinge-ch2-ch3. In some embodiments, the CXCL10, the immunoglobulin molecule or a fragment thereof are of human origin. In some embodiments, the fusion protein further comprises a linker between the WT or mutated CXCL10 and the immunoglobulin or the fragment thereof. The linker may be a stretch of one or more Glycine amino acids (poly G) or a stretch of Glycine and Serine amino acids (poly GS), such as for example, one or more units of GGGGS (SEQ ID No: 7).

In some embodiments, the poly GS includes three units and is GGGGSGGGGSGGGGS (SEQ ID No: 6).

In some embodiments, the fusion protein or the modified CXCL10 is capable of binding to CXCR3 receptor. In some embodiments, the fusion protein is capable of inducing CD8+ T cells. In some embodiments, the modified CXCL10 polypeptide may induce (potentiate) the activity of CD8+ T cells by eliciting the levels of interferon gamma (IFN-g), tumor necrosis factor alpha (TNFa), Granzyme-B, perforin, and Interleukin 2 (IL-2).

In some embodiments, there is provided a method of treating cancer in a subject in need thereof, the method comprising administering to the subject in need thereof a therapeutically amount of the modified CXCL10 polypeptide or the fusion protein of the invention or a pharmaceutical composition comprising the modified CXCL10 polypeptide or the fusion protein of the invention. In some embodiments, there is provided a pharmaceutical composition comprising the modified CXCL10 polypeptide or the fusion protein of the invention and a pharmaceutically acceptable carrier. In some embodiments, the pharmaceutical composition is suitable for use in treating cancer.

In some embodiments, there is provided a nucleic acid molecule encoding the modified CXCL10 polypeptide or the fusion protein of the invention. In some embodiments, there is provided vector comprising the nucleic acid molecule described herein. In some embodiments, the vector is an expression vector, further comprising one or more regulatory sequences.

In some embodiments, the vector or the nucleic acid may be used in treating cancer in a subject in need thereof. In some embodiments, the vector or the nucleic acid may be used in treating cancer in a subject in need thereof. In some embodiments, there is provided a method of treating cancer in a subject in need thereof, the method comprising administering to the subject in need thereof a therapeutically amount of the nucleic acid molecule or the vector of the invention. In some embodiments, there is provided a host cell comprising the nucleic acid molecule of the invention. In some embodiments, there is provided a host cell transformed or transfected with the vector of the invention. In some embodiments, there is provided a host cell comprising the modified CXCL10 polypeptide or the fusion protein of the invention. In some embodiments, there is provided a method of producing the modified CXCL10 polypeptide, the method comprising: (i) culturing the host cells of comprising the nucleic acid or the vector of the invention under conditions such that the polypeptide comprising the modified CXCL10 is expressed; and (ii) optionally recovering the modified CXCL10 from the host cells or from the culture medium.

In some embodiments of the invention, the modified CXCL10 polypeptide described above is linked to an immunoglobulin or to a fragment thereof. In some embodiments of the invention, there is provided a WT CXCL10 polypeptide linked to an immunoglobulin or to a fragment thereof. In some embodiments of the invention, there is provided a WT CXCL10 polypeptide linked to a non-proteinaceous moiety. In some embodiments of the invention, there is provided a modified CXCL10 polypeptide linked to a non-proteinaceous moiety.

In some embodiments of the invention, there is provided a stabilized CXCL10 chemokine which is a CXCL10-Ig fusion polypeptide that optionally includes a poly GS linker.

In some embodiments of the invention, there is provided a modified CXCL10 polypeptide comprising an insertion of one or more tandem repeats of the peptide "GGGGS" SEQ ID No: 7 (four glycines and one serine) at the C-terminus of a corresponding WT CXCL10 polypeptide. The one or more GGGGS units is termed in here poly GS.

In an embodiment of the invention, there is provided a modified CXCL10 polypeptide comprising an insertion of a stretch of one or more units of Glycine and Serine amino acids (poly GS) at the C-terminus of a corresponding WT CXCL10 polypeptide.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIGS. 1A-1D: FIG. 1A shows that CXCL10 inhibits the proliferation/viability rate (XTT assay) of ret melanoma cells when recombinant mouse CXCL10 is added. FIG. 1B shows the same if recombinant human CXCL10 is used. FIG. 1C shows the same when mouse CXCL10-Ig is used. This also indicates for cross-reactivity between mouse and human. Results of four replicates for each concentration are shown as mean±SD. P values are indicated in the graphs. FIG. 1D shows similarity between human (MNQTAILICCLIFLTLSGIQGVPLSRTVRCTCISISNQPVNPRSLEKLEIIPASQFCPRVEI IATMKKKGEKRCLNPESKAIKNLLKAVSKERSKRSP, SEQ ID NO: 48) and murine CXCL10 (MNPSAAVIFCLILLGLSGTQGIPLARTVRCNCIHIDDGPVRMRAIGKLEIIPASLSCPRV EIIATMKKNDEQRCLNPESKTIKNLMKAFSQKRSKRAP, SEQ ID NO: 49), both express Arginine at position 5 that is subjected to PAD induced citrullination.

FIG. 3A shows the development of tumors along time kinetics whereas

FIG. 8A shows a schematic view of the experimental protocol. Three days after ret melanoma line engraftment in either WT or CXCR3KO donor mice CD8+ T cells were isolated from the spleen and transferred ($0.5\times10^6$ cells per mouse) into CXCR3−/− mice 3 days following engraftment with ret melanoma line. All mice were treated twice a week with CXCL10-Ig (200 μg/mouse) or PBS and monitored for primary tumor development (FIG. 8B). On day 20 mice were sacrificed and tumor weight was measured (FIG. 8C). Results are shown as mean (n=5)±SD, and analyzed by one-way ANOVA (*P<0.041).

(FIG. 9A) Tumor size was measured with electronic caliber and calculated according the equation: (length×width×height)×0.52. (FIG. 9B) Kaplan Meier plot survival curve of these groups.

FIG. 10A shows tumor size as mean size+SD (length×width×height)×0.52. FIG. 10B shows scattered analyses on day 17. FIG. 10C shows mortality curve. *P≤0.05 was considered as significant.

DESCRIPTION OF THE DETAILED EMBODIMENTS

Figure 1A:
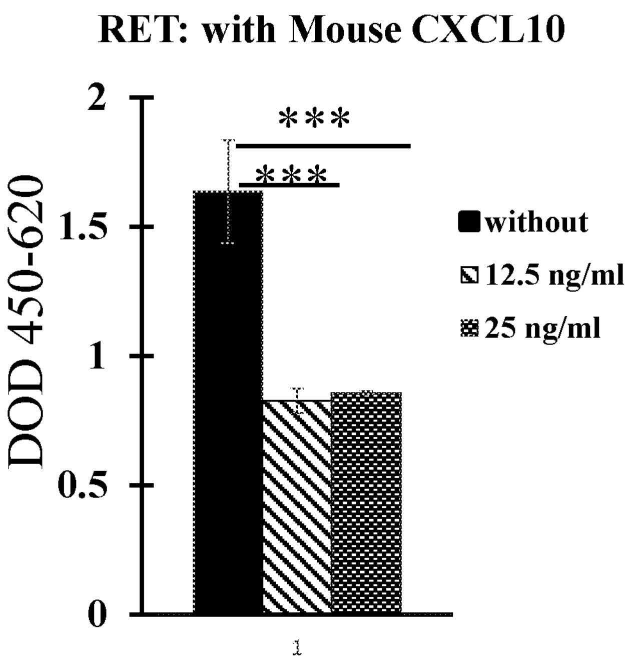
Figure 1B:
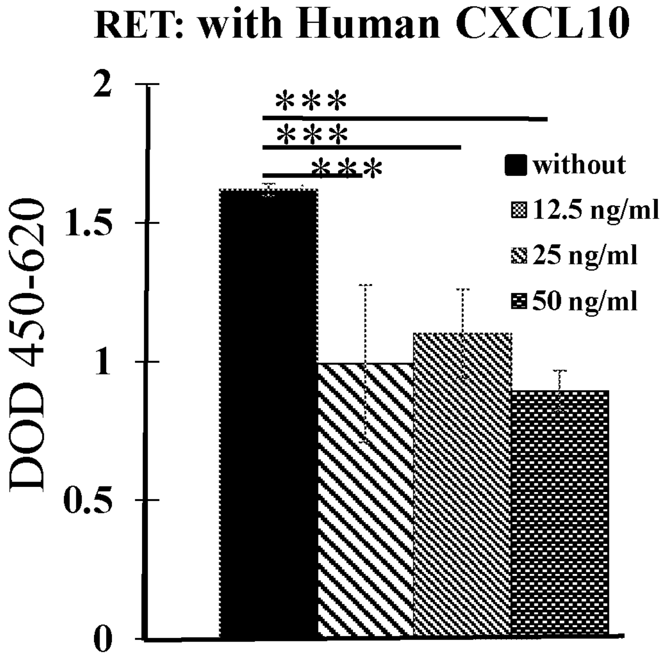
Figure 1C:
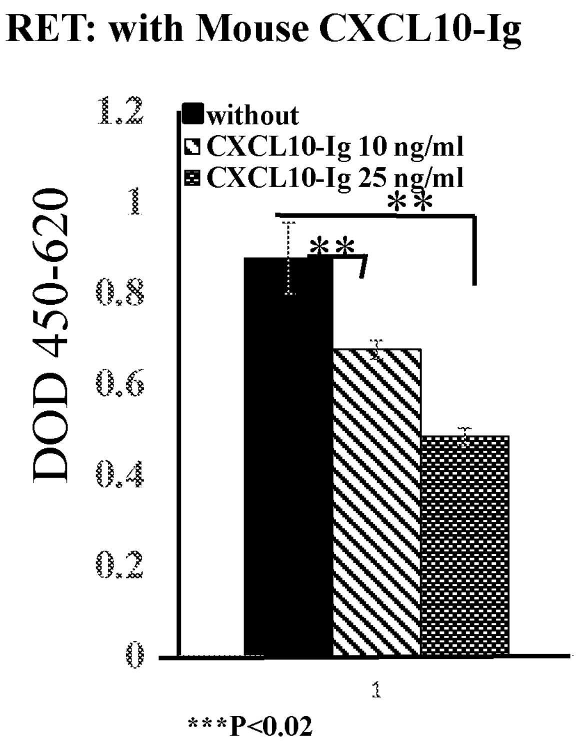

The principles, uses, and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

DEFINITIONS

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "polynucleotide molecules", "oligonucleotide", "polynucleotide", "nucleic acid" and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded (ss), double stranded (ds), triple stranded (ts), or hybrids thereof. The polynucleotides may be, for example, or polynucleotide sequences of DNA or RNA. The DNA or RNA molecules may be, for example, but are not limited to: complementary DNA (cDNA), genomic DNA, synthesized DNA, recombinant DNA, or a hybrid thereof or an RNA molecule such as, for example, mRNA. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions. As used herein, nucleotides (A, G, C or T) and nucleotide sequences are marked in lowercase letters (a, g, c or t).

The terms "polypeptide," "peptide" and "protein" are used interchangeably herein to refer to a polymer of amino acid residues. The terms also apply to amino acid polymers in which one or more amino acid residue is an artificial chemical analogue of a corresponding naturally occurring amino acid, as well as to naturally occurring amino acid polymers. In some embodiments, one or more of amino acid residue in the polypeptide, can contain modification, such as but be not limited only to, glycosylation, phosphorylation or disulfide bond shape. Also provided are conservative amino acid variants of the peptides and protein molecules disclosed herein. Variants according to the invention also may be made that conserve the overall molecular structure of the encoded proteins or peptides. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved. As used herein, Amino acids and peptide sequences are marked using conventional Amino Acid nomenclature (single letter or 3-letters code). For example, amino acid "Serine" may be marked as "Ser" or "S" and amino acid "Cysteine" may be marked as "Cys" or "C".

As referred to herein, the term "complementarity" is directed to base pairing between strands of nucleic acids. As known in the art, each strand of a nucleic acid may be complementary to another strand in that the base pairs between the strands are non-covalently connected via two or three hydrogen bonds. Two nucleotides on opposite complementary nucleic acid strands that are connected by hydrogen bonds are called a base pair. According to the Watson-Crick DNA base pairing, adenine (A or a) forms a base pair with thymine (T or t) and guanine (G or g) with cytosine (C or c). In RNA, thymine is replaced by uracil (U or u). The degree of complementarity between two strands of nucleic acid may vary, according to the number (or percentage) of nucleotides that form base pairs between the strands. For example, "100% complementarity" indicates that all the nucleotides in each strand form base pairs with the complement strand. For example, "95% complementarity" indicates that 95% of the nucleotides in each strand from base pair with the complement strand. The term sufficient complementarity may include any percentage of complementarity from about 30% to about 100%.

The term "construct", as used herein refers to an artificially assembled or isolated nucleic acid molecule which may be comprises of one or more nucleic acid sequences, wherein the nucleic acid sequences may be coding sequences (that is, sequence which encodes for an end product), regulatory sequences, non-coding sequences, or any combination thereof. The term construct includes, for example, vectors, plasmids but should not be seen as being limited thereto. The term "regulatory sequence" in some embodiments, refers to DNA sequences, which are necessary to effect the expression of coding sequences to which they are operably linked (connected/ligated). The nature of the regulatory sequences differs depending on the host cells. For example, in prokaryotes, regulatory/control sequences may include promoter, ribosomal binding site, and/or terminators. For example, in eukaryotes regulatory/control sequences may include promoters, terminators enhancers, trans-activators and/or transcription factors. A regulatory sequence which is "operably linked" to a coding sequence is ligated in such a way that expression of the coding sequence is achieved under suitable conditions. In some embodiments, a "Construct" or a "DNA construct" refer to an artificially assembled or isolated nucleic acid molecule which comprises a coding region of interest and optionally additional regulatory or non-coding sequences.

As used herein, the term "vector" refers to any recombinant polynucleotide construct (such as a DNA construct) that may be used for the purpose of transformation, i.e. the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced. The term "Expression vector" refers to vectors that have the ability to incorporate and express heterologous nucleic acid fragments (such as DNA) in a foreign cell. In other words, an expression vector comprises nucleic acid sequences/fragments (such as DNA, mRNA), capable of being transcribed or expressed in a target cell. Many viral, prokaryotic and eukaryotic expression vectors are known and/or commercially available. Selection of appropriate expression vectors is within the knowledge of those having skill in the art. The expression vectors can include one or more regulatory sequences.

As used herein, a "primer" defines an oligonucleotide which is capable of annealing to (hybridizing with) a target nucleotide sequence, thereby creating a double stranded region which can serve as an initiation point for DNA synthesis under suitable conditions.

As used herein, the term "transformation" refers to the introduction of foreign DNA into cells. The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, injection, and the like, or combinations thereof. The transfection of the cell may be performed on any type of cell, of any origin, such as, for example, human cells, animal cells, plant cells, and the like. The cells may be isolated cells, tissue cultured cells, cell lines, cells present within an organism body, and the like.

The terms "upstream" and "downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

As used herein, the term "treating" includes, but is not limited to one or more of the following: abrogating, ameliorating, inhibiting, attenuating, blocking, suppressing, reducing, delaying, halting, alleviating or preventing symptoms associated with a condition. Each possibility represents a separate embodiment of the present invention. In some embodiments, the condition is a cancer. In some exemplary embodiments, the condition may be selected from, melanoma or metastatic melanoma and the like.

The term "CXCL10" is interchangeable with any alternative name or synonym of this protein known in the art. The term refers to a protein or polypeptide, primarily to a human protein. The term further refers to a nucleic acid encoding for the corresponding polypeptide. The amino acid sequences and encoding nucleotide sequences of CXCL10 are well known in the art. Nucleic acid sequences can be retrieved in public databases like NCBI. In some embodiments, the Homo sapiens Wild Type CXCL10 corresponds to SEQ ID NO: 8.

The term "wild type CXCL10", "WT CXCL10", "naturally occurring CXCL10" and "un-modified CXCL10" may interchangeably be used. The terms refer to the naturally occurring form of CXCL10 (i.e., an endogenous, non-mutated CXCL10 or full-length CXCL10). In some embodiments, the WT-CXCL10 is from a mammalian origin. In some embodiments, the WT-CXCL10 is of human origin. In some embodiments, the WT-CXCL10 of human origin has an amino acid sequence as denoted by SEQ ID NO:8. The polynucleotide sequence as set forth in SEQ ID NO: 9 corresponds to the cDNA encoding human WT CXCL10 as set forth in SEQ ID NO: 8.

As used herein the terms "modified CXCL10", "mutated CXCL10", "non-naturally occurring CXCL10", may interchangeably be used. The terms relate to a mutated/modified form of the corresponding wild-type (WT) or natural form of the CXCL10. In some embodiments, the CXCL10 is of human origin and it is termed "modified hCXCL10", "mutated hCXCL10", "non-naturally occurring hCXCL10" or "modified CXCL10", "mutated CXCL10", "non-naturally occurring CXCL10". In some embodiments, the CXCL10 is of mammalian origin. In some embodiments, the CXCL10 is of human origin. In some embodiments, the modified CXCL10 differs from the corresponding wild type CXCL10 by one mutation or more selected from amino acid substitution(s), insertion(s) and/or deletions(s). In some embodiments of the invention, the modified CXCL10 polypeptide may be conjugated to an Ig, i.e CXCL10-Ig or to a fragment of an Ig molecule. In some embodiments of the invention, the Ig or the fragment thereof is without limitation, IgG-Fc: hinge-ch2-ch3 or protein-G purification reto hinge-CH1-CH2-CH3. Such a conjugated or chimeric modified CXCL10 polypeptide is also defined here as modified CXCL10 polypeptide and may be interchangeably defined as modified CXCL10-Ig polypeptide. In some embodiments, the modified CXCL10 polypeptide may be linked to a non-proteinaceous moiety (e.g., PEG), with or without a linker. In some embodiments, the modified CXCL10 is a modified CXCL10 polypeptide, in which an additional amino acid has been inserted at the N terminus position of a corresponding WT CXCL10.

Figure 8A:
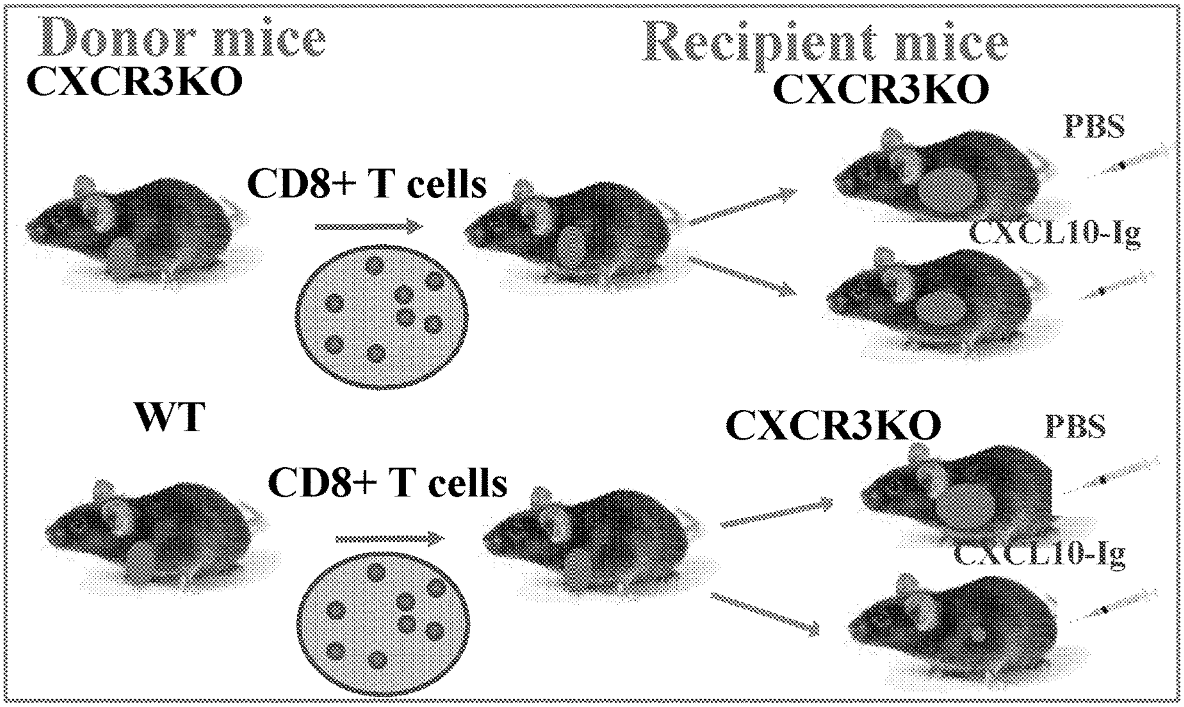
FIGS. 8A-8C show that CXCL10-Ig restrains melanoma in CXCR3KO mice following reconstitution with CD8+ T cells from WT but not CXCR3KO mice.
Figure 8B:
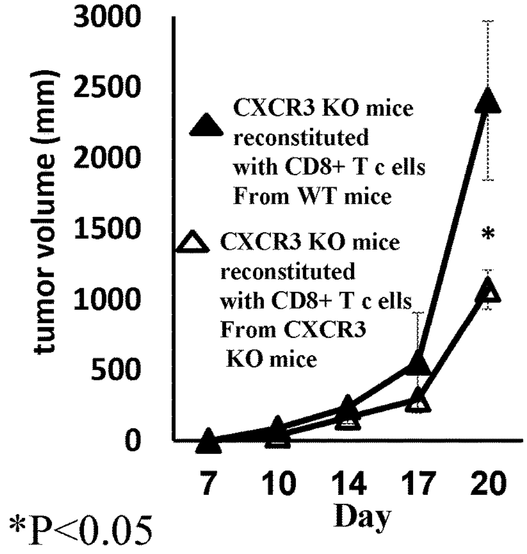
Figure 8C:
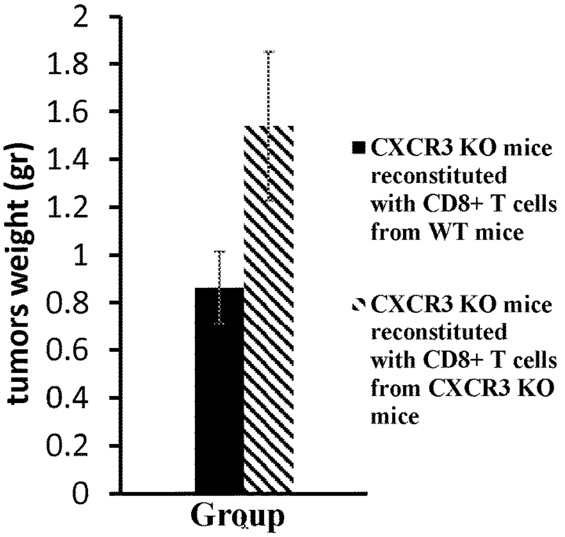

One of the approaches for cancer therapy is based on enhancing anti-cancer immunity, particularly the response of CD8+ T cells (also known as immunotherapy). The examples of the invention show that the chemokine CXCL10 and mutants thereof could be used to treat or suppress cancer diseases. The examples of the invention further show that the chemokine CXCL10 and modified CXCL10 polypeptide enhance the response of CD8+T as specified in details in FIG. 8 showing that reconstituting CXCR3KO mice with CD8+ T cells that were isolated from the spleen of CXCR3+ donor mice (or CXCR3KO mice as control) three days after tumor engraftment and transferred ($0.5\times10^6$ cells per mouse) to recipients developing melanoma. It is shown that fusion protein CXCL10-Ig effectively treated mice reconstituted with donor CD8+ T cells from CXCR3+ mice (FIG. 8). In some embodiments of the invention, CXCL10, CXCL10-Ig and modified CXCL10 polypeptide thereof induce anti-tumor CD8+ T cells, and by so doing suppress cancer diseases, for example without limitation, melanoma. In some embodiments of the invention, CXCL10, CXCL10-Ig and modified CXCL10 polypeptide thereof limit or prevent metastatic melanoma. In some embodiments of the invention, CXCL10, CXCL10-Ig and modified CXCL10 polypeptide thereof limit, suppress or prevent cancer diseases, such as without limitation, colorectal cancer, ovarian carcinoma, osteosarcoma (OS), melanoma, lung cancer, head and neck cancer and hepatocellular carcinoma (HCC).

In some embodiments of the invention, there is provided a CXCL10-Ig based fusion protein. In some embodiments of the invention, there is provided a CXCL10-Ig based fusion protein, wherein the CXCL10 is a modified CXCL10 polypeptide.

In some embodiments, the modified CXCL10 polypeptide or the modified CXCL10-Ig polypeptide the invention is capable of binding to CXCR3 receptor.

In some embodiments, the modified CXCL10 polypeptide or the modified CXCL10-Ig polypeptide is capable of inducing CD8+ T cells. By "inducing" it is meant the potentiates the activity of the cells including but not limited to cytotoxicity.

In some embodiments, the sequence of a human CXCL10 (WT) is as set forth below at SEQ ID No. 8:
hCXCL10 WT
Protein Sequence of hCXCL10 WT:

```
                                       (SEQ ID No: 8)
MNQTAILICCLIFLTLSGIQGVPLSRTVRCTCISISNQPVNPRS

LEKLEIIPASQFCPRVEIIATMKKKGEKRCLNPESKAIKNLLKA

VSKERSKRSP
```

In some embodiments, the sequence of the cDNA encoding human CXCL10 (WT) is as set forth below at SEQ ID No: 9:

cDNA Sequence of hCXCL10 WT

```
                                       (SEQ ID No: 9)
atgaatcaaa ctgccattct gatttgctgc

cttatctttc tgactctaag

tggcattcaa ggagtacctc tctctagaac

tgtacgctgt acctgcatca gcattagtaa

tcaacctgtt aatccaaggt ctttagaaaa

acttgaaatt attcctgcaa gccaattttg

tccacgtgtt gagatcattg ctacaatgaa

aaagaagggt gagaagagat gtctgaatcc

agaatcgaag gccatcaaga atttactgaa

agcagttagc aaggaaaggt ctaaaagatc

tcct
```

In some embodiments, there is provided a human modified CXCL10 polypeptide, in which an additional amino acid was inserted at the N-terminus position of a corresponding WT CXCL10, wherein the resulted CXCL10 is resistant to DPP4 and has an anti-cancer activity. According to some embodiments of the invention, the sequence of such a modified CXCL10 polypeptide is as set forth in SEQ ID No: 1, wherein X refers to any amino acid:
hCXCL10-Insertion of X (X Refers to any Amino Acid) at N-Terminus

```
                                       (SEQ ID No: 1)
MNQTAILICCLIFLTLSGIQGXVPLSRTVRCTCISISNQPVNPRS

LEKLEIIPASQFCPRVEIIATMKKKGEKRCLNPESKAIKNLLKAV

SKERSKRSP.
```

In some embodiments, there is provided a human modified CXCL10 polypeptide, in which glutamine was inserted at the N-terminus position of a corresponding WT CXCL10. According to some embodiments of the invention, the sequence of such a modified CXCL10 polypeptide is as set forth in SEQ ID No: 2:
hGln-CXCL10: Insertion of Gln at hCXCL10 N-Terminus
Protein Sequence of hGln-CXCL10:

```
                                       (SEQ ID No: 2)
MNQTAILICCLIFLTLSGIQGQVPLSRTVRCTCISISNQPVNPRS

LEKLEIIPASQFCPRVEIIATMKKKGEKRCLNPESKAIKNLLKAV

SKERSKRSP.
```

In some embodiments, the sequence of the cDNA encoding a hCXCL10 having an insertion of Gln at N-terminus is as set forth below at SEQ ID No: 10:
cDNA Sequence of hGln-CXCL10:

```
                                       (SEQ ID No: 10)
atgaatcaaa ctgccattct gatttgctgc

cttatctttc tgactctaag

tggcattcaa ggaCAAgtacctc tctctagaac
```

-continued

```
tgtacgctgt acctgcatca gcattagtaa
tcaacctgtt aatccaaggt ctttagaaaa
acttgaaatt attcctgcaa gccaattttg
tccacgtgtt gagatcattg ctacaatgaa
aaagaagggt gagaagagat gtctgaatcc
agaatcgaag gccatcaaga atttactgaa
agcagttagc aaggaaaggt ctaaaagatc
tcct
```

In some embodiments, there is provided a human modified CXCL10 polypeptide, in which asparagine was inserted at the N-terminus position of a corresponding WT CXCL10. According to some embodiments of the invention, the sequence of such a modified CXCL10 polypeptide is as set forth in SEQ ID No: 3.

hAsn-CXCL10: Insertion of Asn at hCXCL10 N-Terminus (SEQ ID No: 3)

Protein Sequence of hAsn-CXCL10:

MNQTAILICCLIFLTLSGIQGNVPLSRTVRCTCISISNQPVNPRS
LEKLEIIPASQFCPRVEIIATMKKKGEKRCLNPESKAIKNLLKAV
SKERSKRSP cDNA Sequence of hAsn-CXCL10 (SEQ ID No: 11)

(SEQ ID No: 11)

atgaatcaaa ctgccattct gatttgctgc
cttatctttc tgactctaag
tggcattcaa ggaAACgtacctc tctctagaac
tgtacgctgt acctgcatca gcattagtaa
tcaacctgtt aatccaaggt ctttagaaaa
acttgaaatt attcctgcaa gccaattttg
tccacgtgtt gagatcattg ctacaatgaa
aaagaagggt gagaagagat gtctgaatcc
agaatcgaag gccatcaaga atttactgaa
agcagttagc aaggaaaggt ctaaaagatc
tcct In some embodiments, there is provided a human modified CXCL10 polypeptide, in which proline was inserted at the N-terminus position of a corresponding WT CXCL10. According to some embodiments of the invention, the sequence of such a modified CXCL10 polypeptide is as set forth in SEQ ID No: 4.

hPro-CXCL10: HCXCL10-Insertion of Pro at N-Terminus (SEQ ID No: 4)

Protein Sequence of hPro-CXCL10

MNQTAILICCLIFLTLSGIQGPVPLSRTVRCTCISISNQPVNPRS
LEKLEIIPASQFCPRVEIIATMKKKGEKRCLNPESKAIKNLLKAV
SKERSKRSP cDNA sequence of hPro-CXCL10 (SEQ ID No:12)

(SEQ ID No: 12)

atgaatcaaa ctgccattct gatttgctgc
cttatctttc tgactctaag
tggcattcaa ggaCCCgtacctc tctctagaac
tgtacgctgt acctgcatca gcattagtaa
tcaacctgtt aatccaaggt ctttagaaaa
acttgaaatt attcctgcaa gccaattttg
tccacgtgtt gagatcattg ctacaatgaa
aaagaagggt gagaagagat gtctgaatcc
agaatcgaag gccatcaaga atttactgaa
agcagttagc aaggaaaggt ctaaaagatc
tcct In some embodiments, the CXCL10 or the modified CXCL10 polypeptide includes an IgG-Fc: hinge-ch2-ch3. In some embodiments, the IgG-Fc: hinge-ch2-ch3 is a human IgG-Fc: hinge-ch2-ch3 denoted by SEQ ID No: 5.

hIgG-Fc: Hinge-CH2-CH3 SEQ ID No: 5.

Protein Sequence of hIgG-Fc: Hinge-CH2-CH3:

```
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPGK
```

cDNA Sequence of hIgG-Fc: Hinge-CH2-CH3 (SEQ ID No: 13)

(SEQ ID No: 13)

```
gagcccaaatcttgtgacaaaactcacacatgcccaccgtgcccagcac
ctgaactcctggggggaccgtcagtcttcctcttccccccaaaacccaa
ggacaccctcatgatctcccggacccctgaggtcacatgcgtggtggtg
gacgtgagccacgaagaccctgaggtcaagttcaactggtacgtggacg
gcgtggaggtgcataatgccaagacaaagccgcgggaggagcagtacaa
cagcacgtaccgtgtggtcagcgtcctcaccgtcctgcaccaggactgg
ctgaatggcaaggagtacaagtgcaaggtctccaacaaagccctcccag
cccccatcgagaaaaccatctccaaagccaaagggcagccccgagaacc
acaggtgtacaccctgcccccatcccgggaggagatgaccaagaaccag
gtcagcctgacctgcctggtcaaaggcttctatcccagcgacatcgccg
tggagtgggagagcaatgggcagccggagaacaactacaagaccacgcc
tcccgtgctggactccgacggctccttcttcctctatagcaagctcacc
gtggacaagagcaggtggcagcaggggaacgtcttctcatgctccgtga
tgcatgaggctctgcacaaccactacacgcagaagagcctctccctgtc
cccgggtaaa
```

In some embodiments, the human CXCL10 or the modified CXCL10 polypeptide includes a human IgG-Fc sequence or fragment thereof resulting in CXCL10-Ig based fusion protein or modified CXCL10-Ig polypeptide.

According to some embodiments of the invention, the administration of the mouse CXCL10-Ig based fusion protein or modified CXCL10-Ig polypeptide suppresses melanoma development in Ret transgenic mice transferred model.

According to some embodiments of the invention, the in vivo half-life of mouse or human CXCL10 is regulated, by citrullination (arginine to citrulline) at position #5 induced by peptidylarginine deiminase (PAD).

In some embodiments of the invention there is provided a modified CXCL10 polypeptide resistant to peptidylarginine deiminase (PAD) induced citrullination comprising an amino acid replacement at a position corresponding to position 5 in a wild type CXCL10 protein wherein an arginine at position #5 of the mutated CXCL10 is substituted with another amino acid. The another amino acid is in some embodiments, lysine or histidine and the sequence of the modified CXCL10 is as set forth of any one of sequences SEQ ID No: 14 or SEQ ID No: 15.

According to some embodiments of the invention, the in vivo half-life of mouse or human CXCL10 is regulated, by citrullination (arginine to citrulline) at position #5 counted after the single peptide sequence after induced by peptidylarginine deiminase (PAD).

Accordingly, in some embodiments of the invention, there is provided a mouse or human modified CXCL10 polypeptide that is resistant to PAD induced citrullination. In some embodiments, the arginine at position 5 of the a CXCL10 is substituted with a similarly charged basic amino acid (in some embodiments, lysine or histidine).

According to some embodiments of the invention, the sequence of such a human modified CXCL10 polypeptide is as set forth in SEQ ID No:15:

hCXCL10-R26H-hCXCL10-Substitution Arg at Position 26 to His

Protein Sequence of hCXCL10-R26H:

(SEQ ID No: 15)
MNQTAILICCLIFLTLSGIQGVPLSHTVRCTCISISNQPVNPRSLEKLE
IIPASQFCPRVEIIATMKKKGEKRCLNPESKAIKNLLKAVSKERSKRSP cDNA Sequence of the hCXCL10-R26H SEQ ID No: 16

(SEQ ID No: 16)
atgaatcaaa ctgccattct gatttgctgc cttatctttc
tgactctaag tggcattcaa ggagtacctc tctctcacac
tgtacgctgt acctgcatca gcattagtaa tcaacctgtt
aatccaaggt ctttagaaaa acttgaaatt attcctgcaa
gccaattttg tccacgtgtt gagatcattg ctacaatgaa
aaagaagggt gagaagagat gtctgaatcc agaatcgaag
gccatcaaga atttactgaa agcagttagc aaggaaaggt
ctaaaagatc tcct According to some embodiments of the invention, the sequence of such a human modified CXCL10 polypeptide is set forth in SEQ ID No: 6:

hCXCL10-subR26K: Substitution of Arg at Position 26 to Lys

Protein Sequence of CXCL10-subR26K:

(SEQ ID No: 14)
MNQTAILICCLIFLTLSGIQGVPLSKTVRCTCISISNQPVNPRSLEKLE
IIPASQFCPRVEIIATMKKKGEKRCLNPESKAIKNLLKAVSKERSKRSP

In some embodiments, the sequence of the cDNA encoding hCXCL10 substitution Arg5 to Lys5 is as set forth below at SEQ ID No. 17:

cDNA Sequence of CXCL10-subR26K (SEQ ID No: 17)
atgaatcaaa ctgccattct gatttgctgc cttatctttc
tgactctaag tggcattcaa ggagtacctc tctctaagac
tgtacgctgt acctgcatca gcattagtaa tcaacctgtt
aatccaaggt ctttagaaaa acttgaaatt attcctgcaa
gccaattttg tccacgtgtt gagatcattg ctacaatgaa
aaagaagggt gagaagagat gtctgaatcc agaatcgaag
gccatcaaga atttactgaa agcagttagc aaggaaaggt
ctaaaagatc tcct In some embodiments of the invention, there is provided a modified hCXCL10 polypeptide that includes a poly G or poly GS chain. In some embodiments, there is provided a modified CXCL10 polypeptide comprising an insertion of a stretch of one or more Glycine amino acids (poly G) or a stretch of Glycine and Serine amino acids (poly GS), such as GGGGS (SEQ ID No. 7) at the C-terminus of a corresponding WT CXCL10 polypeptide.

As used herein, a “stretch” of “amino acids” means a plurality of amino acids arranged in a chain, each of which is joined to a preceding amino acid by a peptide bond. The amino acids of the chain may be naturally or non-naturally occurring, or may comprise a mixture thereof. In some embodiments, each “stretch”, contains two or more amino acid residues that are adjacent to each other or close to each other (ie, in the primary or tertiary structure of the amino acid sequence).

In some embodiments of the invention, a poly GS linker may be added to the CXCL10 or the mutated CXCL10. In some embodiments, a sequence of one or more repeated GGGGS (SEQ ID No: 7) is added. In some embodiments of the invention, a polyG or poly GS linker may be added to the CXCL10. The linkers, two or more units of GGGGS (SEQ ID No: 7), GGGGSGGGGSGGGGS (SEQ ID No: 6) and the like as described in Shen, Z et al Anal Chem 77, 6834-6842 (2005), and Kim et al PloS one 9, e113442 (2014) are inserted between the Fc and the C-terminus part of CXCL10. In some embodiments, a linker comprises of at least two glycine is added. In some embodiments, a linker comprises between 2-20 glycine is added. In some embodiments, a sequence of GGGGSGGGGSGGGGS (SEQ ID No: 6) is added and the sequence of the hCXCL10 with poly GS is as follows (SEQ ID No: 18).

hCXCL10-polyGS-Addition of Poly GS at the c-Terminus of hCXCL10 (No Stop Codon) Protein Sequence hCXCL10-polyGS:

(SEQ ID No: 18)
MNQTAILICCLIFLTLSGIQGVPLSRTVRCTCISISNQPVNPRSLEKLE

-continued

```
IIPASQFCPRVEIIATMKKKGEKRCLNPESKAIKNLLKAVSKERSKRSP

GGGGSGGGGSGGGGS
```

In some embodiments, the sequence of the cDNA encoding hCXCL10 with poly GS (no stop codon) is as set forth below at SEQ ID No: 19:

cDNA Sequence of hCXCL10-polyGS:

```
                                        (SEQ ID No: 19)
atgaatcaaa ctgccattct gatttgctgc cttatctttc

tgactctaag tggcattcaa ggagtacctc tctctagaac

tgtacgctgt acctgcatca gcattagtaa tcaacctgtt

aatccaaggt ctttagaaaa acttgaaatt attcctgcaa

gccaattttg tccacgtgtt gagatcattg ctacaatgaa

aaagaagggt gagaagagat gtctgaatcc agaatcgaag

gccatcaaga atttactgaa agcagttagc aaggaaaggt

ctaaaagatctcct GGCGGAGGTGGCTCTGGCGGTGGCGGATCGGGCG

GAGGTGGCTCT
```

In some embodiments of the invention, any of the human modified CXCL10 polypeptide of the invention may be conjugated to an immunoglobulin (Ig) or a fragment thereof. The Ig may be in some embodiments, IgG. In some embodiments of the invention, the Ig or the fragment thereof is without limitation, IgG-Fc: hinge-ch2-ch3.

For example, in various embodiments, the peptides are linked to the Fc portion of an immunoglobulin (e.g., to promote antibody-dependent cellular cytotoxicity (ADCC) and/or complement-dependent cytotoxicity (CDC)). In some embodiments, the CXCL10 is linked to the Fc region of an IgG antibody. In some embodiments, the CXCL10 is linked to the Fc region of a human IgG1, IgG2, IgG3 and IgG4 isotype.

As used herein, "immunoglobulin Fc region" refers to a protein that contains the heavy-chain constant region 2 ($CH_2$) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains of the immunoglobulin, as long as it has an effect substantially similar to or better than that of the native form. Also, it may be a region having a deletion in a relatively long portion of the amino acid sequence of CH2 and/or CH3. That is, the immunoglobulin Fc region of the present invention may include 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region is safe for use as a drug carrier because it is a biodegradable polypeptide that is metabolized in vivo. Also, the immunoglobulin Fc region has a relatively low molecular weight, as compared to the whole immunoglobulin molecules, and thus, it is advantageous in terms of preparation, purification and yield of the conjugate. The immunoglobulin Fc region does not contain a Fab fragment, which is highly non-homogenous due to different amino acid sequences according to the antibody subclasses, and thus it can be expected that the immunoglobulin Fc region may greatly increase the homogeneity of substances and be less antigenic in blood.

The immunoglobulin Fc region may be derived from humans or other animals including cows, goats, swine, mice, rabbits, hamsters, rats and guinea pigs, and preferably, humans. In addition, the immunoglobulin Fc region may be an Fc region that is derived from IgG, IgA, IgD, IgE, and IgM, or made by combinations thereof or hybrids thereof. Preferably, it is derived from IgG or IgM, which are among the most abundant proteins in human blood, and most preferably, from IgG which is known to enhance the half-lives of ligand-binding proteins.

IgG is divided into IgG1, IgG2, IgG3 and IgG4 subclasses, and the present invention includes combinations and hybrids thereof. Preferred are IgG1 and IgG4 subclasses, and most preferred is the Fc region of IgG4 rarely having effector functions such as CDC (complement dependent cytotoxicity).

Meanwhile, the immunoglobulin Fc region may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. Here, the removal of sugar chains from an Fc region results in a sharp decrease in binding affinity to the complement (clq) and a decrease or loss in antibody-dependent cell-mediated cytotoxicity or complement-dependent cytotoxicity, thereby not inducing unnecessary immune responses in vivo. In this regard, an immunoglobulin Fc region in a deglycosylated or aglycosylated form may be more suitable to the object of the present invention as a drug carrier.

As used herein, "deglycosylation" means to enzymatically remove sugar moieties from an Fc region, and "aglycosylation" means that an Fc region is produced in an unglycosylated form by a prokaryote, preferably, *E. coli.*

Further, the immunoglobulin Fc region of the present invention includes a sequence derivative (mutant) thereof as well as a native amino acid sequence. An amino acid sequence derivative has a sequence that is different from the native amino acid sequence due to deletion, insertion, non-conservative or conservative substitution of one or more amino acid residues, or combinations thereof. For example, in IgG Fc, amino acid residues known to be important in binding, at positions 214 to 238, 297 to 299, 318 to 322, or 327 to 331, may be used as a suitable target for modification. In addition, other various derivatives are possible, including derivatives having a deletion of a region capable of forming a disulfide bond, a deletion of several amino acid residues at the N-terminus of a native Fc form, or an addition of a methionine residue to the N-terminus of a native Fc form. Furthermore, to remove effector functions, a deletion may occur in a complement-binding site, such as a Clq-binding site and an ADCC (antibody dependent cell mediated cytotoxicity) site. Techniques of preparing such sequence derivatives of the immunoglobulin Fc region are disclosed in WO 97/34631 and WO 96/32478.

The Fc region, if desired, may be modified by phosphorylation, sulfation, acrylation, glycosylation, methylation, farnesylation, acetylation, amidation or the like. In some embodiments of the invention, the CXCL10 of the invention and IgG and/or any other protein that may be used for extending the half-life of the variant of the invention in the serum are linked by a linker. In Some embodiments of the invention, the linker is a sequence of between 2-30 amino acids. In Some embodiments of the invention, the linker is a sequence of between 2-20 amino acids. In Some embodiments of the invention, the linker is a sequence of between 2-10 amino acids. In some embodiments, the linker is a poly G or poly GS linker as described herein.

An example of a heterologous amino acid sequence which may be used in accordance with this aspect of the present invention is an immunoglobulin amino acid sequence, such as the hinge and Fc regions of an immunoglobulin heavy domain (see U.S. Pat. No. 6,777,196). The immunoglobulin moiety in the chimeras of this aspect of the present invention may be obtained from IgG1, IgG2, IgG3 or IgG4 subtypes, IgA, IgE, IgD or IgM, as further discussed hereinbelow.

Typically, in such fusions the chimeric molecule will retain at least functionally active hinge and CH2 and CH3 domains of the constant region of an immunoglobulin heavy chain. Fusions can also be generated to the C-terminus of the Fc portion of a constant domain, or immediately N-terminus to the CH1 of the heavy chain or the corresponding region of the light chain.

Though it may be possible to conjugate the entire heavy chain constant region to the CXCL10 amino acid sequence of the present invention, it is preferable to fuse shorter sequences. For example, a sequence beginning at the hinge region upstream of the papain cleavage site, which defines IgG Fc chemically; residue 216, taking the first residue of heavy chain constant region to be 114, or analogous sites of other immunoglobulins, may be used in the fusion. In a particular embodiment, the CXCL10 amino acid sequence is fused to the hinge region and CH2 and CH3, or to the CH1, hinge, CH2 and CH3 domains of an IgG2, or IgG3 heavy chain (see U.S. Pat. No. 6,777,196).

For example, a nucleic acid sequence encoding a CXCL10 peptide of the present invention is ligated in frame to an immunoglobulin cDNA sequence. It will be appreciated that, ligation of genomic immunoglobulin fragments can also be used. In this case, fusion requires the presence of immunoglobulin regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques.

In some embodiments, the invention further envisages inclusion of the modified CXCL10 or the WT CXCL10 in a complex where it is attached to proteinaceous (e.g., heterologous amino acid sequence) or each of which being capable of prolonging the half-life of the composition while in circulation. Such a molecule is highly stable, resistant to in-vivo proteaolytic activity and may be produced using common solid phase synthesis. Further recombinant techniques may still be used, whereby the recombinant peptide product is subjected to in-vitro modification (e.g., PEGylation as further described herein below).

The phrase "non-proteinaceous moiety" as used herein refers to a molecule that is attached to the above-described CXCL10 amino acid sequences. According to some embodiments the non-proteinaceous moiety may be a polymer or a co-polymer (synthetic or natural). Non-limiting examples of the non-proteinaceous moiety of the present invention include polyethylene glycol (PEG) or derivative thereof, Polyvinyl pyrrolidone (PVP), albumin, divinyl ether and maleic anhydride copolymer (DIVEMA); polysialic acid (PSA) and/or poly(styrene comaleic anhydride) (SMA). Additionally, complexes which can protect CXCL10 or modified CXCL10 from the environment and thus keep its stability may be used, including, for example, liposomes or micelles are also included in the invention.

According to some embodiments of the invention, modified CXCL10 or the WT CXCL10 of the invention is attached to a non-proteinaceous moiety, which may act as a sustained-release enhancing agent. Exemplary sustained-release enhancing agents include, but are not limited to hyaluronic acid (HA), alginic acid (AA), polyhydroxyethyl methacrylate (Poly-HEMA), glyme and polyisopropylacrylamide.

Attaching the modified CXCL10 or the WT CXCL10 to other non-amino acid agents may be by covalent linking or by non-covalent complexion, for example, by complexion to a hydrophobic polymer, which can be degraded or cleaved producing a compound capable of sustained release; The association may be by the entrapment of the amino acid sequence within the other component (liposome, micelle) or the impregnation of the amino acid sequence within a polymer to produce the final peptide of the invention.

In some embodiments, the PEG derivative is N-hydroxysuccinimide (NHS) esters of PEG carboxylic acids, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. PEG-maleimide, PEG-vinylsulfone (VS), PEG-acrylate (AC) or PEG-orthopyridyl disulfide may be also used.

In some embodiments of the invention, there is provided a pharmaceutical composition comprising a modified CXCL10 polypeptide as described herein, optionally conjugated to an Ig, with or without a linker which may be a poly G or a sequence of one, two, three or more repeated units of GGGGS (SEQ ID No: 7), i.e. poly GS, and a pharmaceutically acceptable carrier. In some embodiments, the modified CXCL10 polypeptide or the WT CXCL10 are linked to the non-proteinaceous moiety or the proteinaceous moiety as described above In some embodiments of the invention, there is provided a pharmaceutical composition comprising a modified CXCL10 polypeptide as described herein, optionally conjugated to an Ig, with or without a linker which may be a poly G, poly GS or a sequence of two or more repeated GGGGS (SEQ ID No: 7), and a pharmaceutically acceptable carrier.

In some embodiments of the invention, there is provided a method of treating cancer comprising the step of administering to a subject in need a pharmaceutical composition comprising a modified CXCL10 polypeptide as described herein, optionally conjugated to an Ig, with or without a linker, and a pharmaceutically acceptable carrier.

In some embodiments of the invention, the cancer is melanoma or metastatic melanoma.

In some embodiments of the invention, the mutated human CXCL10 that are optionally conjugated to Ig, may be administered to a subject in need in combination with another anticancer treatment, such as without being limited, such as, cellular or non cellular immunotherapy like immune checkpoint inhibitors, cancer vaccines, conjugated antibodies, bi-specific T cell engagers, bi-specific NK cell engagers, oncolytic viruses, 'eat me' signals, 'find me' signals or others, or non-immunotherapy anti-cancer treatments, including chemotherapy, biological therapies like, for example, tyrosine kinase inhibitors, anti-angiogenic therapy, hormonal therapy, radiotherapy or surgery.

In some embodiments of the invention, there is provided a nucleic acid molecule encoding the modified CXCL10 polypeptide of the invention.

In some embodiments of the invention, there is provided a vector comprising the nucleic acid molecule encoding the modified CXCL10 polypeptide of the invention. The vector being an expression vector, further comprising one or more regulatory sequences.

In some embodiments of the invention, the nucleic acid molecule of the invention or the vector may be used for use in treating cancer in a subject in need thereof.

In some embodiments of the invention, there is provided a host cell comprising the nucleic acid molecule of the invention. In some embodiments of the invention, there is provided host cells transformed or transfected with the vector of the invention. In some embodiments of the invention, there is provided a host cell comprising the modified CXCL10 polypeptide of the invention.

In some embodiments of the invention, there is provided a method of producing the modified CXCL10 polypeptide, the method comprising: (i) culturing the host cells comprising the nucleic acids encoding the modified CXCL10 polypeptide under conditions such that the polypeptide comprising the modified CXCL10 is expressed; and (ii) recovering the modified CXCL10 from the host cells or from the culture medium.

In the experiments, the following mouse sequences are used:

In some embodiments, the sequence of a mouse CXCL10 (WT) is as set forth below at SEQ ID No: 20:
mCXCL10 WT

```
                                        (SEQ ID No: 20)
MNPSAAVIFCLILLGLSGTQGIPLARTVRCNCIHIDDGPVRMRAIGKLE
IIPASLSCPRVEIIATMKKNDEQRCLNPESKTIKNLMKAFSQKRSKRAP
```

In some embodiments, the CXCL10 or the mutant thereof includes a mouse mIgG-Fc: hinge-CH2-CH3, which is as follows:

```
                                        (SEQ ID No: 21)
VPRDCGCKPCICTVPEVSSVFIFPPKPKDVLTITLTPKVTCVVVDISKD

DPEVQFSWFVDDVEVHTAQTQPREEQFNSTFRSVSELPIMHQDCLNGKE

FKCRVNSAAFPAPIEKTISKTKGRPKAPQVYTIPPPKEQMAKDKVSLTC

MITDFFPEDITVEWQWNGQPAENYKNTQPIMDTDGSYFVYSKLNVQKSN

WEAGNTFTCSVLHEGLHNHHTEKSLSHSPGK
```

According to some embodiments of the invention, the administration of the mouse CXCL10-Ig based fusion protein or mutant or a modified CXCL10 linked to a non-proteinaceous moiety thereof suppresses melanoma development in ret transgenic mice transferred model.

According to some embodiments of the invention, the in vivo half-life of mouse CXCL10 is regulated, by citrullination (arginine to citrulline) at position #5 induced by peptidylarginine deiminase (PAD).

Accordingly, in some embodiments of the invention, there is provided a mouse CXCL10 mutant that is resistant to PAD induced citrullination. In some embodiments, the arginine at position 5 of the a CXCL10 is substituted with a similarly charged basic amino acid (in some embodiments, lysine or histidine) and by so doing with the required modifications for human treatment, generates a highly potent pharmaceutical composition for cancer immunotherapy.

According to some embodiments of the invention, the sequence of such a mouse CXCL10 mutant is as follows:
mCXCL10-subR26H-Substitution of Arg at Position 26 to His

```
                                        (SEQ ID No: 22)
MNPSAAVIFCLILLGLSGTQGIPLAHTVRCNCIHIDDGPVRMRAIGKLE
IIPASLSCPRVEIIATMKKNDEQRCLNPESKTIKNLMKAFSQKRSKRAP
```

According to some embodiments of the invention, the sequence of such a mouse CXCL10 mutant is as follows:
mCXCL10-R26H: Substitution of Arg at Position 26 to Lys

```
                                        (SEQ ID No: 23)
MNPSAAVIFCLILLGLSGTQGIPLAKTVRCNCIHIDDGPVRMRAIGKLE
IIPASLSCPRVEIIATMKKNDEQRCLNPESKTIKNLMKAFSQKRSKRAP
```

In some embodiments, there is provided a mouse CXCL10 mutant, in which glutamine was inserted at the N-terminus position. According to some embodiments of the invention, the sequence of such a CXCL10 mutant is as follows:
mGlnCXCL10-Insertion of Gln at N-Terminus

```
                                        (SEQ ID No: 24)
MNPSAAVIFCLILLGLSGTQGQIPLARTVRCNCIHIDDGPVRMRAIGKLE
IIPASLSCPRVEIIATMKKNDEQRCLNPESKTIKNLMKAFSQKRSKRAP
```

In some embodiments of the invention, a polyG or poly GS linker may be added to the CXCL10. In some embodiments, a sequence of two or more repeated GGGGS (SEQ ID No: 7) is added. In some embodiments, as a sequence of two or more repeated GGGGS is added. In some embodiments, as a sequence of GGGGSGGGGSGGGGS (SEQ ID No: 6) is added.
mCXCL10-polyGS: Addition of Poly GS at the C-Terminus (No Stop Codon):

```
                                        (SEQ ID No: 25)
MNPSAAVIFCLILLGLSGTQGIPLARTVRCNCIHIDDGPVRMRAIGKLE
IIPASLSCPRVEIIATMKKNDEQRCLNPESKTIKNLMKAFSQKRSKRAP
GGGGSGGGGSGGGGS
```

In some embodiments of the invention, any of the mouse modified CXCL10 may be conjugated to Ig or part thereof, such as without limitation, mIgG-Fc: hinge-ch2-ch3.

In some embodiments, there is provided a mouse nucleic acid sequence encoding the mCXCL10-Poly GS.
cDNA of mCXCL10-polyGS

```
                                        (SEQ ID No: 26)
ATGAACCCAAGTGCTGCCGTCATTTTCTGCCTCATCCTGCTGGGTCTGA

GTGGGACTCAAGGGATCCCTCTCGCAAGGACGGTCCGCTGCAACTGCAT

CCATATCGATGACGGGCCAGTGAGAATGAGGGCCATAGGGAAGCTTGAA

ATCATCCCTGCGAGCCTATCCTGCCCACGTGTTGAGATCATTGCCACGA

TGAAAAAGAATGATGAGCAGAGATGTCTGAATCCGGAATCTAAGACCAT
```

-continued

```
CAAGAATTTAATGAAAGCGTTTAGCCAAAAAAGGTCTAAAAGGGCTCCT

GGCGGAGGTGGCTCTGGCGGTGGCGGATCGGGCGGAGGTGGCTCT.
```

In some embodiments, there is provided a mouse nucleic acid sequence encoding the mCXCL10 insGln (21_22) cDNA of mGlnCXCL10 (21_22)

```
                                     (SEQ ID No: 27)
ATGAACCCAAGTGCTGCCGTCATTTTCTGCCTCATCCTGCTGGGTCTG

AGTGGGACTCAAGGGCAAATCCCTCTCGCAAGGACGGTCCGCTGCAAC

TGCATCCATATCGATGACGGGCCAGTGAGAATGAGGGCCATAGGGAAG

CTTGAAATCATCCCTGCGAGCCTATCCTGCCCACGTGTTGAGATCATT

GCCACGATGAAAAAGAATGATGAGCAGAGATGTCTGAATCCGGAATCT

AAGACCATCAAGAATTTAATGAAAGCGTTTAGCCAAAAAAGGTCTAAA

AGGGCTCCTC.
```

According to some embodiments, any suitable route of administration to a subject may be used for the nucleic acid, polypeptide or the composition of the present invention, including but not limited to, local and systemic routes. Exemplary suitable routes of administration include, but are not limited to: orally, intra-nasally, parenterally, intravenously, topically, enema or by inhalation. According to another embodiment, systemic administration of the composition is via an injection. For administration via injection, the composition may be formulated in an aqueous solution, for example in a physiologically compatible buffer including, but not limited, to Hank's solution, Ringer's solution, or physiological salt buffer. Formulations for injection may be presented in unit dosage forms, for example, in ampoules, or in multi-dose containers with, optionally, an added preservative.

According to another embodiment, administration systemically is through a parenteral route. According to some embodiments, parenteral administration is administration intravenously, intra-arterially, intramuscularly, intraperitoneally, intradermally, intravitreally, or subcutaneously. Each of the abovementioned administration routes represents a separate embodiment of the present invention. According to another embodiment, parenteral administration is performed by bolus injection. According to another embodiment, parenteral administration is performed by continuous infusion. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art. The preferred mode of administration will depend upon the particular indication being treated and will be apparent to one of skill in the art.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to another embodiment, administration systemically is through an enteral route. According to another embodiment, administration through an enteral route is buccal administration. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

According to some embodiments, suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

In some embodiments, if desired, disintegrating agents, such as cross-linked polyvinyl pyrrolidone, agar, or alginic acid or a salt thereof, such as sodium alginate, may be added. Capsules and cartridges of, for example, gelatin, for use in a dispenser may be formulated containing a powder mix of the composition of the invention and a suitable powder base, such as lactose or starch.

According to some embodiments, solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

In some embodiments, liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term “enteral coating”, as used herein, refers to a coating which controls the location of composition absorption within the digestive system. Non-limiting examples for materials used for enteral coating are fatty acids, waxes, plant fibers or plastics.

According to some embodiments, administering is administering topically. According to some embodiments, the composition is formulated for topical administration. The term “topical administration”, as used herein, refers to administration to body surfaces. Non-limiting examples of formulations for topical use include cream, ointment, lotion, gel, foam, suspension, aqueous or cosolvent solutions, salve and sprayable liquid form. Other suitable topical product forms for the compositions of the present invention include, for example, emulsion, mousse, lotion, solution and serum.

According to some embodiments, the administration may include any suitable administration regime, depending, inter alia, on the medical condition, patient characteristics, administration route, and the like. In some embodiments, administration may include administration twice daily, every day, every other day, every third day, every fourth day, every fifth day, once a week, once every second week, once every third week, once every month, and the like.

According to some embodiments, the modified CXCL10 polypeptide, the nucleic acid encoding the same, and/or the composition comprising the polypeptide or the nucleic acid molecules, when used for used for treating cancer may be used in combination with other therapeutic agents. The components of such combinations may be administered sequentially or simultaneously/concomitantly in separate or combined pharmaceutical formulations by any suitable administration route.

According to some embodiments, there are provided kits comprising the modified CXCL10 polypeptide and/or the nucleic acid molecule encoding the same and/or the composition as disclosed herein. Such a kit can be used, for example, in the treatment of cancer.

In the description and claims of the application, the words “include” and “have”, and forms thereof, are not limited to members in a list with which the words may be associated.

As used herein, the term comprising includes the term consisting of.

As used herein, the term “about” may be used to specify a value of a quantity or parameter (e.g. the length of an element) to within a continuous range of values in the neighborhood of (and including) a given (stated) value. According to some embodiments, “about” may specify the value of a parameter to be between 80% and 120% of the given value. According to some embodiments, “about” may specify the value of a parameter to be between 90% and 110% of the given value. According to some embodiments, “about” may specify the value of a parameter to be between 95% and 105% of the given value.

As used herein, according to some embodiments, the terms “substantially” and “about” may be interchangeable.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

The following provides additional amino acid and nucleic acid sequences of modified human CXCL10 (hCXCL10), as discussed herein.

Variants of hCXCL10-Ig hGlnCXCL10-Ig: Insertion of Gln at the N-Terminus of hCXCL10 (1-78) Protein Sequence of hGlnCXCL10-Ig:

(SEQ ID No: 28)

MNQTAILICCLIFLTLSGIQGQVPLSRTVRCTCISISNQPVNPRSLEK

LEIIPASQFCPRVEIIATMKKKGEKRCLNPESKAIKNLLKAVSKERSK

RSP*VPRDCGCKPCICTVPEVSSVFIFPPKPKDVLTITLTPKVTCVVVD*

*ISKDDPEVQFSWFVDDVEVHTAQTQPREEQFNSTFRSVSELPIMHQDC*

*LNGKEFKCRVNSAAFPAPIEKTISKTKGRPKAPQVYTIPPPKEQMAKD*

*KVSLTCMITDFFPEDITVEWQWNGQPAENYKNTQPIMDTDGSYFVYSK*

*LNVQKSNWEAGNTFTCSVLHEGLHNHHTEKSLSHSPGK* cDNA Sequence of hGInCXCL10-Ig (1-78)

(SEQ ID No: 29)

atgaatcaaactgccattctgatttgctgccttatctttctgactcta agtggcattcaaggacaagtacctctctctagaactgtacgctgtacc tgcatcagcattagtaatcaacctgttaatccaaggtctttagaaaaa cttgaaattattcctgcaagccaattttgtccacgtgttgagatcatt gctacaatgaaaaagaagggtgagaagagatgtctgaatccagaatcg aaggccatcaagaatttactgaaagcagttagcaaggaaaggtctaaa agatctcctGTGCCCAGGGATTGTGGTTGTAAGCCTTGCATATGTACA

GTCCCAGAAGTATCATCTGTCTTCATCTTCCCCCCAAAGCCCAAGGAT

GTGCTCACCATTACTCTGACTCCTAAGGTCACGTGTGTTGTGGTAGAC

ATCAGCAAGGATGATCCCGAGGTCCAGTTCAGCTGGTTTGTAGATGAT

GTGGAGGTGCACACAGCTCAGACGCAACCCCGGGAGGAGCAGTTCAAC

AGCACTTTCCGCTCAGTCAGTGAACTTCCCATCATGCACCAGGACTGC

CTCAATGGCAAGGAGTTCAAATGCAGGGTCAACAGTGCAGCTTTCCCT

GCCCCCATCGAGAAAACCATCTCCAAAACCAAAGGCAGACCGAAGGCT

CCACAGGTGTACACCATTCCACCTCCCAAGGAGCAGATGGCCAAGGAT

AAAGTCAGTCTGACCTGCATGATAACAGACTTCTTCCCTGAAGACATT

ACTGTGGAGTGGCAGTGGAATGGGCAGCCAGCGGAGAACTACAAGAAC

ACTCAGCCCATCATGGACACAGATGGCTCTTACTTCGTCTACAGCAAG

CTCAATGTGCAGAAGAGCAACTGGGAGGCAGGAAATACTTTCACCTGC

TCTGTGTTACATGAGGGCCTGCACAACCACCATACTGAGAAGAGCCTC

TCCCACTCTCCTGGTAAA hAsn-CXCL10-Ig: Insertion of Asn at the N-Terminus of hCXCL10

Protein Sequence:

(SEQ ID No: 30)

MNQTAILICCLIFLTLSGIQGNVPLSRTVRCTCISISNQPVNPRSLEK

LEIIPASQFCPRVEIIATMKKKGEKRCLNPESKAIKNLLKAVSKERSK

RSP*VPRDCGCKPCICTVPEVSSVFIFPPKPKDVLTITLTPKVTCVVVD*

*ISKDDPEVQFSWFVDDVEVHTAQTQPREEQFNSTFRSVSELPIMHQDC*

*LNGKEFKCRVNSAAFPAPIEKTISKTKGRPKAPQVYTIPPPKEQMAKD*

*KVSLTCMITDFFPEDITVEWQWNGQPAENYKNTQPIMDTDGSYFVYSK*

*LNVQKSNWEAGNTFTCSVLHEGLHNHHTEKSLSHSPGK* cDNA Sequence of hAsnCXCL10-Ig (SEQ ID No: 31)

atgaatcaaactgccattctgatttgctgccttatctttctgactcta agtggcattcaaggaaatgtacctctctctagaactgtacgctgtacc tgcatcagcattagtaatcaacctgttaatccaaggtctttagaaaaa cttgaaattattcctgcaagccaattttgtccacgtgttgagatcatt gctacaatgaaaaagaagggtgagaagagatgtctgaatccagaatcg aaggccatcaagaatttactgaaagcagttagcaaggaaaggtctaaa agatctcctGTGCCCAGGGATTGTGGTTGTAAGCCTTGCATATGTACA

GTCCCAGAAGTATCATCTGTCTTCATCTTCCCCCCAAAGCCCAAGGAT

GTGCTCACCATTACTCTGACTCCTAAGGTCACGTGTGTTGTGGTAGAC

ATCAGCAAGGATGATCCCGAGGTCCAGTTCAGCTGGTTTGTAGATGAT

GTGGAGGTGCACACAGCTCAGACGCAACCCCGGGAGGAGCAGTTCAAC

AGCACTTTCCGCTCAGTCAGTGAACTTCCCATCATGCACCAGGACTGC

CTCAATGGCAAGGAGTTCAAATGCAGGGTCAACAGTGCAGCTTTCCCT

GCCCCCATCGAGAAAACCATCTCCAAAACCAAAGGCAGACCGAAGGCT

CCACAGGTGTACACCATTCCACCTCCCAAGGAGCAGATGGCCAAGGAT

AAAGTCAGTCTGACCTGCATGATAACAGACTTCTTCCCTGAAGACATT

ACTGTGGAGTGGCAGTGGAATGGGCAGCCAGCGGAGAACTACAAGAAC

ACTCAGCCCATCATGGACACAGATGGCTCTTACTTCGTCTACAGCAAG

CTCAATGTGCAGAAGAGCAACTGGGAGGCAGGAAATACTTTCACCTGC

TCTGTGTTACATGAGGGCCTGCACAACCACCATACTGAGAAGAGCCTC

TCCCACTCTCCTGGTAAA hCXCL10polyGS-Ig: Addition of Poly GS at the C-Terminus of the CXCL10

Protein Sequence:

(SEQ ID No: 32)

MNQTAILICCLIFLTLSGIQGVPLSRTVRCTCISISNQPVNPRSLEKL

EIIPASQFCPRVEIIATMKKKGEKRCLNPESKAIKNLLKAVSKERSKR

SPGGGGSGGGGSGGGGS*VPRDCGCKPCICTVPEVSSVFIFPPKPKDVL*

*TITLTPKVTCVWDISKDDPEVQFSWFVDDVEVHTAQTQPREEQFNSTF*

*RSVSELPIMHQDCLNGKEFKCRVNSAAFPAPIEKTISKTKGRPKAPQV*

-continued

*YTIPPPKEQMAKDKVSLTCMITDFFPEDITVEWQWNGQPAENYKNTQP*

*IMDTDGSYFVYSKLNVQKSNWEAGNTFTCSVLHEGLHNHHTEKSLSHS*

*PGK* cDNA Sequence of hCXCL10-polyGS-Ig (SEQ ID No: 33)

atgaatcaaactgccattctgatttgctgccttatctttctgactcta agtggcattcaaggagtacctctctctagaactgtacgctgtacctgc atcagcattagtaatcaacctgttaatccaaggtctttagaaaaactt gaaattattcctgcaagccaattttgtccacgtgttgagatcattgct acaatgaaaaagaagggtgagaagagatgtctgaatccagaatcgaag gccatcaagaatttactgaaagcagttagcaaggaaaggtctaaaaga tctcctGGCGGAGGTGGCTCTGGCGGTGGCGGATCGGGCGGAGGTGGC

TCT*GTGCCCAGGGATTGTGGTTGTAAGCCTTGCATATGTACAGTCCCA*

*GAAGTATCATCTGTCTTCATCTTCCCCCCAAAGCCCAAGGATGTGCTC*

*ACCATTACTCTGACTCCTAAGGTCACGTGTGTTGTGGTAGACATCAGC*

*AAGGATGATCCCGAGGTCCAGTTCAGCTGGTTTGTAGATGATGTGGAG*

*GTGCACACAGCTCAGACGCAACCCCGGGAGGAGCAGTTCAACAGCACT*

*TTCCGCTCAGTCAGTGAACTTCCCATCATGCACCAGGACTGCCTCAAT*

*GGCAAGGAGTTCAAATGCAGGGTCAACAGTGCAGCTTTCCCTGCCCCC*

*ATCGAGAAAACCATCTCCAAAACCAAAGGCAGACCGAAGGCTCCACAG*

*GTGTACACCATTCCACCTCCCAAGGAGCAGATGGCCAAGGATAAAGTC*

AGTCTGACCTGCATGATAACAGACTTCTTCCCTGAAGACATTACTGTG

*GAGTGGCAGTGGAATGGGCAGCCAGCGGAGAACTACAAGAACACTCAG*

*CCCATCATGGACACAGATGGCTCTTACTTCGTCTACAGCAAGCTCAAT*

*GTGCAGAAGAGCAACTGGGAGGCAGGAAATACTTTCACCTGCTCTGTG*

*TTACATGAGGGCCTGCACAACCACCATACTGAGAAGAGCCTCTCCCAC*

*TCTCCTGGTAAA*

The following provides the amino acid sequences and nucleic acid sequences of wild type or modified mice CXCL10, as discussed herein.

Variants of Mouse CXCL10-Ig mGlnCXCL10-Ig: Insertion of Gln at the N-Terminus of CXCL10

Protein Sequence of mGlnCXCL10-Ig:

(SEQ ID No: 34)

MNPSAAVIFCLILLGLSGTQGQIPLARTVRCNCIHIDDGPVRMRAIGK

LEIIPASLSCPRVEIIATMKKNDEQRCLNPESKTIKNLMKAFSQKRSK

RAP*VPRDCGCKPCICTVPEVSSVFIFPPKPKDVLTITLTPKVTCVVVD*

*ISKDDPEVQFSWFVDDVEVHTAQTQPREEQFNSTFRSVSELPIMHQDC*

*LNGKEFKCRVNSAAFPAPIEKTISKTKGRPKAPQVYTIPPPKEQMAKD*

*KVSLTCMITDFFPEDITVEWQWNGQPAENYKNTQPIMDTDGSYFVYSK*

*LNVQKSNWEAGNTFTCSVLHEGLHNHHTEKSLSHSPGK* cDNA Sequence mGlnCXCL10-Ig (SEQ ID No: 35)
ATGAACCCAAGTGCTGCCGTCATTTTCTGCCTCATCCTGCTGGGTCTG
AGTGGGACTCAAGGGCAAATCCCTCTCGCAAGGACGGTCCGCTGCAAC
TGCATCCATATCGATGACGGGCCAGTGAGAATGAGGGCCATAGGGAAG
CTTGAAATCATCCCTGCGAGCCTATCCTGCCCACGTGTTGAGATCATT
GCCACGATGAAAAAGAATGATGAGCAGAGATGTCTGAATCCGGAATCT
AAGACCATCAAGAATTTAATGAAAGCGTTTAGCCAAAAAAGGTCTAAA
AGGGCTCCT*GTGCCCAGGGATTGTGGTTGTAAGCCTTGCATATGTACA*
*GTCCCAGAAGTATCATCTGTCTTCATCTTCCCCCCAAAGCCCAAGGAT*
*GTGCTCACCATTACTCTGACTCCTAAGGTCACGTGTGTTGTGGTAGAC*
*ATCAGCAAGGATGATCCCGAGGTCCAGTTCAGCTGGTTTGTAGATGAT*
*GTGGAGGTGCACACAGCTCAGACGCAACCCCGGGAGGAGCAGTTCAAC*
*AGCACTTTCCGCTCAGTCAGTGAACTTCCCATCATGCACCAGGACTGC*
*CTCAATGGCAAGGAGTTCAAATGCAGGGTCAACAGTGCAGCTTTCCCT*
*GCCCCCATCGAGAAAACCATCTCCAAAACCAAAGGCAGACCGAAGGCT*
*CCACAGGTGTACACCATTCCACCTCCCAAGGAGCAGATGGCCAAGGAT*
*AAAGTCAGTCTGACCTGCATGATAACAGACTTCTTCCCTGAAGACATT*
*ACTGTGGAGTGGCAGTGGAATGGGCAGCCAGCGGAGAACTACAAGAAC*
*ACTCAGCCCATCATGGACACAGATGGCTCTTACTTCGTCTACAGCAAG*
*CTCAATGTGCAGAAGAGCAACTGGGAGGCAGGAAATACTTTCACCTGC*
*TCTGTGTTACATGAGGGCCTGCACAACCACCATACTGAGAAGAGCCTC*
*TCCCACTCTCCTGGTAAA* mAsnCXCL10-Ig: Insertion of Asn at the N-Terminus of the mCXCL10
Protein Sequence of mAsnCXL10-Ig (SEQ ID No: 36)
MNPSAAVIFCLILLGLSGTQGNIPLARTVRCNCIHIDDGPVRMRAIGK
LEIIPASLSCPRVEIIATMKKNDEQRCLNPESKTIKNLMKAFSQKRSK
RAP*VPRDCGCKPCICTVPEVSSVFIFPPKPKDVLTITLTPKVTCVVVD*
*ISKDDPEVQFSWFVDDVEVHTAQTQPREEQFNSTFRSVSELPIMHQDC*
*LNGKEFKCRVNSAAFPAPIEKTISKTKGRPKAPQVYTIPPPKEQMAKD*
*KVSLTCMITDFFPEDITVEWQWNGQPAENYKNTQPIMDTDGSYFVYSK*
*LNVQKSNWEAGNTFTCSVLHEGLHNHHTEKSLSHSPGK* cDNA Sequence mAsnCXCL10-Ig (SEQ ID No: 37)
ATGAACCCAAGTGCTGCCGTCATTTTCTGCCTCATCCTGCTGGGTCTG
AGTGGGACTCAAGGGAATATCCCTCTCGCAAGGACGGTCCGCTGCAAC
TGCATCCATATCGATGACGGGCCAGTGAGAATGAGGGCCATAGGGAAG
CTTGAAATCATCCCTGCGAGCCTATCCTGCCCACGTGTTGAGATCATT
GCCACGATGAAAAAGAATGATGAGCAGAGATGTCTGAATCCGGAATCT -continued AAGACCATCAAGAATTTAATGAAAGCGTTTAGCCAAAAAAGGTCTAAA
AGGGCTCCT*GTGCCCAGGGATTGTGGTTGTAAGCCTTGCATATGTACA*
*GTCCCAGAAGTATCATCTGTCTTCATCTTCCCCCCAAAGCCCAAGGAT*
*GTGCTCACCATTACTCTGACTCCTAAGGTCACGTGTGTTGTGGTAGAC*
*ATCAGCAAGGATGATCCCGAGGTCCAGTTCAGCTGGTTTGTAGATGAT*
*GTGGAGGTGCACACAGCTCAGACGCAACCCCGGGAGGAGCAGTTCAAC*
*AGCACTTTCCGCTCAGTCAGTGAACTTCCCATCATGCACCAGGACTGC*
*CTCAATGGCAAGGAGTTCAAATGCAGGGTCAACAGTGCAGCTTTCCCT*
*GCCCCCATCGAGAAAACCATCTCCAAAACCAAAGGCAGACCGAAGGCT*
*CCACAGGTGTACACCATTCCACCTCCCAAGGAGCAGATGGCCAAGGAT*
*AAAGTCAGTCTGACCTGCATGATAACAGACTTCTTCCCTGAAGACATT*
*ACTGTGGAGTGGCAGTGGAATGGGCAGCCAGCGGAGAACTACAAGAAC*
*ACTCAGCCCATCATGGACACAGATGGCTCTTACTTCGTCTACAGCAAG*
*CTCAATGTGCAGAAGAGCAACTGGGAGGCAGGAAATACTTTCACCTGC*
*TCTGTGTTACATGAGGGCCTGCACAACCACCATACTGAGAAGAGCCTC*
*TCCCACTCTCCTGGTAAA* mCXCL10polyGS-Ig: Addition of polyGS at the C-Terminus of the mCXCL10 Protein Sequence of mCXCL10polyG-Ig (SEQ ID No: 38)
MNPSAAVIFCLILLGLSGTQGIPLARTVRCNCIHIDDGPVRMRAIGKL
EIIPASLSCPRVEIIATMKKNDEQRCLNPESKTIKNLMKAFSQKRSKR
APGGGGSGGGGSGGGGS *VPRDCGCKPCICTVPEVSSVFIFPPKPKDVL*
*TITLTPKVTCVVVDISKDDPEVQFSWFVDDVEVHTAQTQPREEQFNST*
*FRSVSELPIMHQDCLNGKEFKCRVNSAAFPAPIEKTISKTKGRPKAPQ*
*VYTIPPPKEQMAKDKVSLTCMITDFFPEDITVEWQWNGQPAENYKNTQ*
*PIMDTDGSYFVYSKLNVQKSNWEAGNTFTCSVLHEGLHNHHTEKSLSH*
*SPGK* cDNA Sequence of mCXCL10polyG-Ig (SEQ ID No: 39)
ATGAACCCAAGTGCTGCCGTCATTTTCTGCCTCATCCTGCTGGGTCTG
AGTGGGACTCAAGGGATCCCTCTCGCAAGGACGGTCCGCTGCAACTGC
ATCCATATCGATGACGGGCCAGTGAGAATGAGGGCCATAGGGAAGCTT
GAAATCATCCCTGCGAGCCTATCCTGCCCACGTGTTGAGATCATTGCC
ACGATGAAAAAGAATGATGAGCAGAGATGTCTGAATCCGGAATCTAAG
ACCATCAAGAATTTAATGAAAGCGTTTAGCCAAAAAAGGTCTAAAAGG
GCTCCTGGCGGAGGTGGCTCTGGCGGTGGCGGATCGGGCGGAGGTGGC
TCTGTGCCCAGGGATTGTGGTTGTAAGCCTTGCATATGTACAGTCCCA
*GAAGTATCATCTGTCTTCATCTTCCCCCCAAAGCCCAAGGATGTGCTC*
*ACCATTACTCTGACTCCTAAGGTCACGTGTGTTGTGGTAGACATCAGC*
*AAGGATGATCCCGAGGTCCAGTTCAGCTGGTTTGTAGATGATGTGGAG*

-continued

*GTGCACACAGCTCAGACGCAACCCCGGGAGGAGCAGTTCAACAGCACT*

*TTCCGCTCAGTCAGTGAACTTCCCATCATGCACCAGGACTGCCTCAAT*

*GGCAAGGAGTTCAAATGCAGGGTCAACAGTGCAGCTTTCCCTGCCCCC*

*ATCGAGAAAACCATCTCCAAAACCAAAGGCAGACCGAAGGCTCCACAG*

*GTGTACACCATTCCACCTCCCAAGGAGCAGATGGCCAAGGATAAAGTC*

*AGTCTGACCTGCATGATAACAGACTTCTTCCCTGAAGACATTACTGTG*

*GAGTGGCAGTGGAATGGGCAGCCAGCGGAGAACTACAAGAACACTCAG*

CCCATCATGGACACAGATGGCTCTTACTTCGTCTACAGCAAGCTCAAT

*GTGCAGAAGAGCAACTGGGAGGCAGGAAATACTTTCACCTGCTCTGTG*

*TTACATGAGGGCCTGCACAACCACCATACTGAGAAGAGCCTCTCCCAC*

*TCTCCTGGTAAA*

Mouse IgG1-Fc (Hinge Region-CH2-CH3) Protein Sequence (SEQ ID No: 40)

VPRDCGCKPCICTVPEVSSVFIFPPKPKDVLTITLTPKVTCVVVDISK

DDPEVQFSWFVDDVEVHTAQTQPREEQFNSTFRSVSELPIMHQDCLNG

KEFKCRVNSAAFPAPIEKTISKTKGRPKAPQVYTIPPPKEQMAKDKVS

LTCMITDFFPEDITVEWQWNGQPAENYKNTQPIMDTDGSYFVYSKLNV

QKSNWEAGNTFTCSVLHEGLHNHHTEKSLSHSPGK cDNA Sequence Mouse IgG1-Fc (Hinge Region-CH2-CH3)

(SEQ ID No: 41)

GTGCCCAGGGATTGTGGTTGTAAGCCTTGCATATGTACAGTCCCAGAA

GTATCATCTGTCTTCATCTTCCCCCCAAAGCCCAAGGATGTGCTCACC

ATTACTCTGACTCCTAAGGTCACGTGTGTTGTGGTAGACATCAGCAAG

GATGATCCCGAGGTCCAGTTCAGCTGGTTTGTAGATGATGTGGAGGTG

CACACAGCTCAGACGCAACCCCGGGAGGAGCAGTTCAACAGCACTTTC

CGCTCAGTCAGTGAACTTCCCATCATGCACCAGGACTGCCTCAATGGC

AAGGAGTTCAAATGCAGGGTCAACAGTGCAGCTTTCCCTGCCCCCATC

GAGAAAACCATCTCCAAAACCAAAGGCAGACCGAAGGCTCCACAGGTG

TACACCATTCCACCTCCCAAGGAGCAGATGGCCAAGGATAAAGTCAGT

CTGACCTGCATGATAACAGACTTCTTCCCTGAAGACATTACTGTGGAG

TGGCAGTGGAATGGGCAGCCAGCGGAGAACTACAAGAACACTCAGCCC

ATCATGGACACAGATGGCTCTTACTTCGTCTACAGCAAGCTCAATGTG

CAGAAGAGCAACTGGGAGGCAGGAAATACTTTCACCTGCTCTGTGTTA

CATGAGGGCCTGCACAACCACCATACTGAGAAGAGCCTCTCCCACTCT

CCTGGTAAA

EXAMPLES

The Working System

A ret melanoma pre-line overexpressing m-Cherry is used so micro-metastasis could be easily observed in histological sections. Engraftment of these cells (s.c.) leads to rapid tumor development. Its resection leads to metastatic spread. A major target antigen for CD4+ and CD8+ specific effector T cells in this disease is the Tyrosinase-related protein 2 (TRP-2). MHC-I Dextramers to C57Bl/6 mouse TRP-2+ CD8+ T cells are commercially available. To dissect the role of CXCL10 and its mutants and stabilized forms thereof in the in vivo function of tumor specific CD8+ T cells this model is used, including engraftment of ret pre-line cells in immunocompetent CXCR3KO mice reconstituted with CD8+ T cells from WT or CXCR3KO mice.

Experimental Methods

Construction of pSecTag-Ig Vector:

cDNA encoding the constant region of Fc (Hinge-CH2-CH3) of mouse IgG1 was constructed from RNA extracted from mouse splenocytes that were cultured for 96 h in the presence of LPS [FULL NAME] and mIL-4 [FULL NAME]. The primers used for this reaction were 5'CTCGAGGTGCCCAGGGATTGTGGTTG-3' (sense) (SEQ ID No: 42) and 5'-GGGCCCTTTACCA GGAGA GTGGGAGA-3' (anti-sense) (SEQ ID No: 43). The PCR product was then digested with Xho1 and ApaI, and ligated into the mammalian expression/secretion vector pSecTag2/Hygro B (Invitrogen®). Next, the new construct underwent cleavage with Nhe1 and Xho1 to remove the original mouse NF-kappa leader sequence found in the original pSecTag2/Hygro B vector. These two steps revealed a modified pSecTag2/Hygro B vector named pSecTag-Ig lacking a signal peptide and include the Hinge-CH2-CH3 of the mouse IgG1 located immediately before the sequences coding for the c-myc and 5 residues of histidine built in the original pSectag-hygro b vector.

Cloning of the Chemokines into the pSecTag-Ig Vector:

The sequences of chemokines (naïve or mutated sequences) were ordered by Rhenium. The chemokines sequences composed of the original signal peptide, the coding region of the chemokine and the cleavage site sequences of the restriction enzyme Nhe1 (GCTAGC) (SEQ ID No:44) and Xho1 (CTCGAG) (SEQ ID No: 45) at the 5' and 3', correspondently. The chemokines were subcloned into the vector containing the mouse IgG1 fragment after digestion with Nhe1 and xho1. The fused fragments were sequenced by dideoxynucleotide sequencing (Sequenase version 2; Millipore®).

Expression of the Constructs in 293T and CHO-DG-44

The constructs were transfected into HEK-293T for transient expression next were transfected into Chinese hamster ovary dhfr−/− (DG44) cells (provided by L. Chasin, Columbia University, New York, NY). Stable cell lines producing the chemokines were generated in the DG-44. The production of the chemokines improved by selection with gradually increasing concentrations of methotrexate. The fusion protein was purified from the culture medium by a Nickle-column Ni-NTA (Thermo-Scientific®).

Animal Model.

All animal experiments were conducted according to the approved Technion ethic committee guidelines (Technion animal experimentation protocol No: IL-085-06-2017). C57BL/6 male mice (WT) were purchased from Harlan (Israel). The breeders of these mice were purchased from JAX® lab (sBar Harbor, Maine). CXCR3−/− mice on the C57BL/6 background were purchased directly from JAX® labs. Mice were maintained in IVC cages under pathogen-free conditions in the animal facility of the Rapport Faculty of Medicine (Technion). At 6 weeks of age, mice were injected subcutaneously on the back with $5\times10^5$ RET cells which were collected with trypsin from cell culture plates washed with PBS and suspended in 200 μl for injection. Mice were separated randomly into the different experiment group post injection and monitored daily for evidence of illness. Tumor diameters were measured using a caliper. Tumor volume was calculated using the formula $\pi/6 \times a \times b^2$, where a represents the longest dimension and b represents the width.

Construction of CXCL10-Ig:

cDNA encoding the constant region (Hinge-CH2-CH3) of mouse IgG1 Fc was generated by RT-PCR on RNA extracted from mouse spleen cells that were cultured for 4 days with LPS and IL-4. The primers used for this reaction were: 5'-ctcgagGTGCCCAGGGATTGTGGTTG-3') (SEQ ID No: 42) and 5'-gggcccTTTACCAGGAGAGTGGGAGA-3') (SEQ ID No: 43). PCR products were digested with XhoI and ApaI and ligated into mammalian expression/secretion vector pSecTag2/Hygro B (Invitrogen® Life Technologies, San Diego, CA). The following sets of primers were used to generate cDNA encoding mouse CXCL-10-Ig from RNA extracted from mouse splenocytes. To generate CDNA encoding mouse CXCL10-Ig 5' gctagcATGAACCCAAGTGCTGCCGTCATTTT 3' (sense) (SEQ ID No: 46) and 5' ctcgagAGGAGCCCTTTTAGACCTTTTTTG 3' (anti-sense) (SEQ ID No: 47) were used. PCR products were digested with NheI and XhoI and subcloned into the vector containing the mouse IgG1 fragment. Since alterations in the amino acid sequence at the N-terminus of chemokines might change their properties, NheI was selected for the cloning procedure, and the original murine kappa chain leader sequence found in pSecTag2/Hygro B was replaced by either mouse CXCL10 leader sequence. The fused fragments were sequenced by dideoxynucleotide sequencing in our facility (Sequins version 2; Upstate Biotechnology).

Expression and Purification of CXCL10-Ig Fusion Proteins:

Expression and purification ofCXCL10-Ig fusion proteins was carried out using CHO dhfr$^{-/-}$ (DG44) cells (kindly provided by Chasin L., Columbia University, NY) according to the method described (Carothers et al., 1989). The fusion proteins were expressed as a disulphide-linked homodimer similar to IgG1, and had a molecular weight of ca. 72 kDa consisting of two identical 36 kDa subunits. The fusion proteins were purified from the culture medium by High-Trap protein G affinity column (GE® Healthcare, Waukesha, WI).

XTT Viability/Proliferation Assay:

Cells were seeded in 96 well plate in RPMI medium supplemented with 10% FCS, Penicillin, Streptomycin and Glutamic acid (10000 cells per well). 24 h after seeding the medium was replaced with fresh one supplemented with different concentration of CXCL10-Ig or with human CXCL10 (PEPROTECH® cat #300-12-SUG) or mouse CXCL10 (PEPROTECH® Cat #250-16-SUG). 24 hours later XTT assay was performed according to the manufactory instruction. (Biological Industries, cat #20-300-1000).

Ex-Vivo Tumor Cell Killing by Splenic CTLs:

CD8+ T cells were separated from spleen of WT control, WT treated with 10 mg/Kg (about 200 μg/mouse) CXCL10-Ig or isotype matched control IgG, and on day 21 post ret challenge CD8+ cells were isolated from the spleen and incubated with CFSE-labeled ret cells for 24 hours in 10:1 ratio following PI staining. The samples were analyzed by flow cytometry and dead/live ratio was calculated.

Flow Cytometry:

For extracellular staining cells were harvested counted and divided to the various staining groups and were Fc blocked (2 μg/106 of FC blocker). Cells were washed with staining buffer and stained (20 min at 4 °C) for extracellular markers using the various antibodies. Stained cells were washed twice and resuspended in 1% PFA. The stained cells were analyzed using FlowJo program after Flow Cytometry acquisition (Cyan Dako, or FACS Caliber BD). For intracellular staining Specified cells were plated at $5\times10^6$ cells/well in stimulation medium and stimulated for 4 hours at standard incubation environment with PMA 1 mM, Ionomycin 10 mM, and 1:1000 diluted golgiplug, cells were then applied for extracellular staining. Intracellular staining procedure was then conducted using BD Biosciences kit according to the manufacturer's instructions. Briefly, cells were then fixed and permeabilized with an appropriate agent. Permeabilized cells were washed and then incubated with intracellular cytokine specific antibodies. Finally, after an additional wash, stained cells were resuspended in PFA 1%. The stained cells were analyzed using FlowJo program after Flow Cytometry acquisition. The following antibodies were used for FACS staining: Anti-CD45 (BIOLEGEND® 103106), Anti-CD8 (BIOLEGEND® 100706), Anti-CD4 (BIOLEGEND® Cat #100412), Anti-IFNγ (BIOLEGEND® Cat #505808), Anti-TNFa (BIOLEGEND® Cat #506306), Anti-GranzymeB (BIOLEGEND® Cat #515405), Anti-CXCR3 (BIOLEGEND® Cat #126529), Anti-CD69 (BIOLEGEND® Cat #104507), MHC Dextramer (Immudex® JD2199-PE).

Cell Separation

Cell separation was conducted using the following cell separation kits: For total T cells (CD3+), EasySep™ mouse T cell isolation kit (STEMCELL, Cat #19851A), for CD8+ T cells, EasySep™ mouse CD8 T cell isolation kit (STEMCELL, Cat #19853A), for CD4+ T cells, EasySep™ mouse CD4 T cell isolation kit (STEMCELL, Cat #19852A) according manufacturer's instructions, successful purification (>96%) was verified by flow cytometry.

Statistical analysis: Statistical analysis was done according to the recommendations of Nature for reporting life sciences research, as specified in legend to figures. For comparison of two groups, linear regression with 95% confidence interval, and unpaired two-tailed Student's T-test were used. One-way ANOVA for paired data was used to determine the significance of the time-response curves. P values of <0.05 were considered statistically significant. For adjustment of the significance value for multiple comparisons, a Bonferroni correction was applied with a corrected significance value of 0.017.

Example 1

Murine CXCL10 and CXCL10-Ig inhibit the proliferation/viability rate (XTT assay) of ret melanoma cells and displays high cross-reactivity between mouse and human: At first, an experiment was made to asses if addition of murine CXCL10 (PEPROTECH®) to cultured ret melanoma cell line affects their proliferation/viability rate (XTT assay)

FIG. 1A shows that CXCL10 inhibits the proliferation/viability rate (XTT assay) of ret melanoma cells and displays high cross-reactivity between mouse and human. At first, it was assessed if CXCL10 inhibits the proliferation/viability rate (XTT assay) of ret melanoma cells and if there is cross-reactivity between human and mouse on this activity (i.e. if human CXCL10 would affect the proliferation/viability rate of murine melanoma line cells). FIG. 1A shows that CXCL10 significantly (P<0.0000058) inhibits proliferation/viability rate of murine melanoma line cells, that this activity is fully cross reactive between mouse and human CXCL10. Furthermore, the fusion protein (CXCL10-Ig, all CXCL10-Ig used in the examples are CXCL10 linked to to IgG-Fc:

hinge-ch2-ch3) acts in very similar manner (FIG. 1A). This implicates that: 1. The murine ret cell line could be used for screening of mouse and human variants 2. Fusion proteins could also be analyzed using this set-up. The results clearly show that CXCL10 directly suppresses tumor growth, and also that there is full cross-reactivity between mouse and human CXCL10, and finally that CXCL10-Ig maintains the biological function of CXCL10 Protocol: ret melanoma tumor cells were cultured in 96 wells plate (104 cells/well) in the presence or absence of commercial human or mouse CXCL10 (PEPROTECH®) or CXCL10-Ig. 48 h later XTT reagent (Beit Hemek) was added at 50 μl per well for 2 h. The absorbance of degraded substrate was measured at wavelength of 450 nanometer minus OD620. Results of 4 replicates for each concentration are shown as mean±SD. P values are indicated in the graphs.

Example 2

Figure 2:
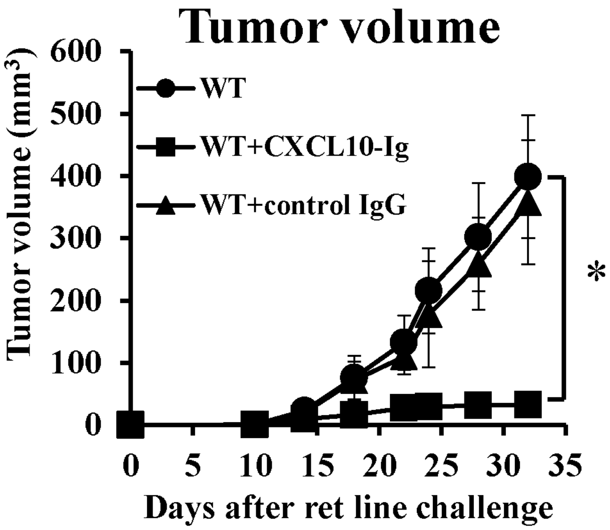
FIG. 2 shows that CXCL10-Ig administration suppresses melanoma development in ret transgenic mice transferred model. Tumor xenograft assay showing reduced melanoma initiation following CXCL10-Ig treatment. C57BL/6 mice were injected s.c with ret transgenic melanoma cell after two days were divided into groups (n=10 each). Only when tumor size reached 10 $mm^3$ mice were treated twice a week with 300 μg CXCL10-Ig, control IgG1 or vehicle (PBS). Tumor size was measured with electronic caliber and calculated according the equation: (length×width×height)×0.52. Results are shown as mean±SD. *, $p<0.001$ FIGS. 3A-3B focuses on dissecting direct and indirect effect of CXCL10-Ig based therapy on melanoma development in ret transgenic mice transferred model. Ten C57BL/6 mice (WT) were administered S.C with $5\times10^5$ ret cells. Two days later, five mice were repeatedly administered (twice a week) with 300 μg CXCL10-Ig and monitored for the development of the primary tumor. Tumor size was measured with electronic caliber and calculated according the equation: (length×width×height)×0.52. Results are shown as mean±SD. *, $p<0.01$.
Figure 3A:
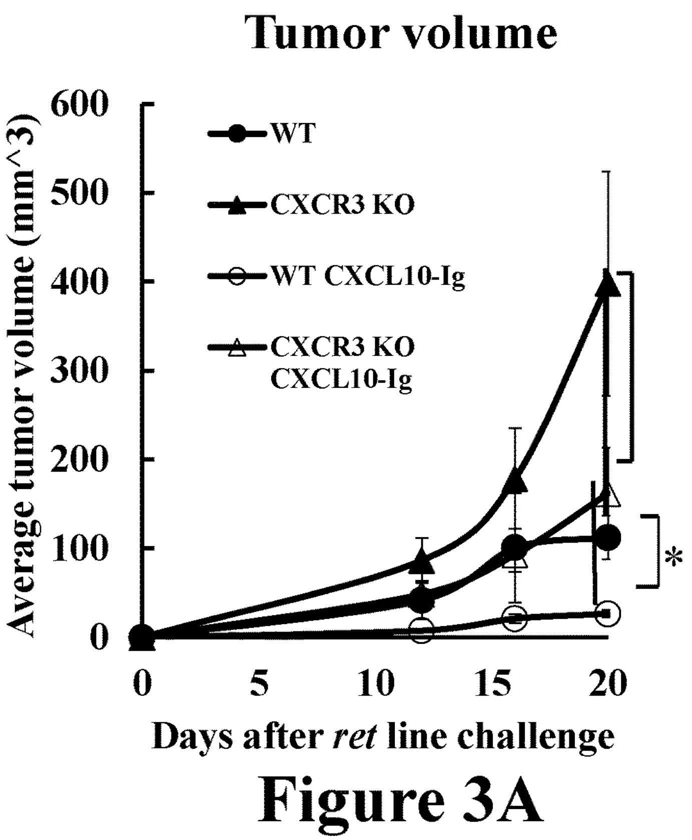
Figure 3B:
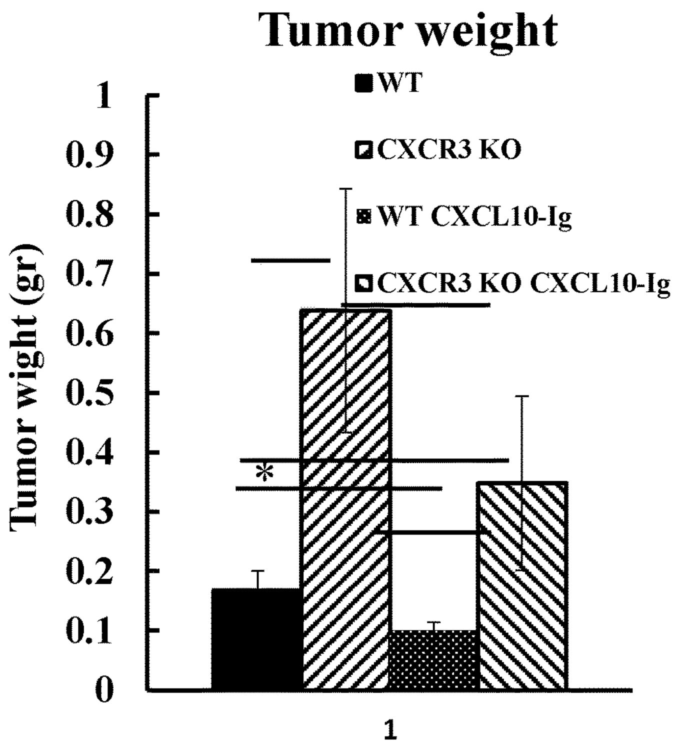
FIG. 3B shows tumor weight when the experiment has been terminated (day 20).
Figure 4A:
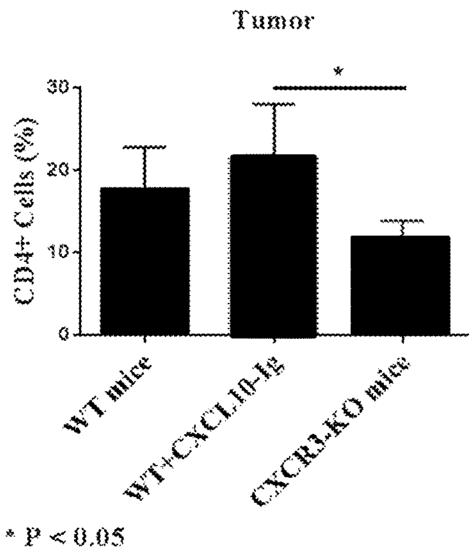
FIGS. 4A-4F show that peripheral administration of CXCL10-Ig enhances CD8+ T cell infiltration to the tumor site. Ten C57BL/6 (WT) and five CXCR3-KO mice were administered s.c with $10^5$ ret melanoma cells. When WT tumors reached size of 2-3 mm, five WT mice were administrated with 10 mg/Kg (about 200 μg/mouse) of CXCL10-Ig, or isotype matched control IgG twice a week, and tumors were harvested at day 21 post tumor challenge. Percentage of CD4+, CD8+ and FOXP3+ T cells in the tumor (FIGS. 4A, 4B and 4C) and spleen (FIGS. 4D, 4E and 4F) were analyzed in the three groups using standard flow cytometry methods. Results are shown as mean±SD.
Figure 4B:
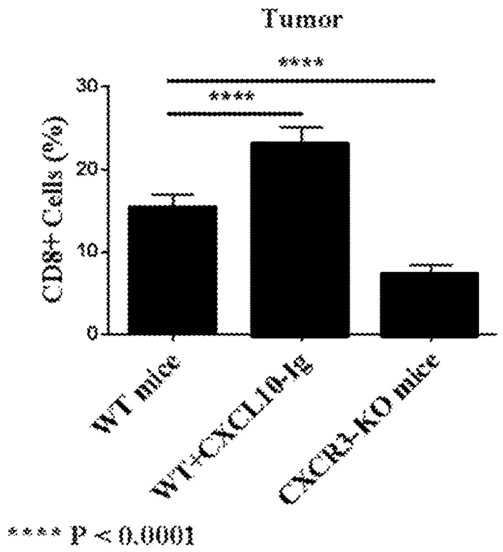
Figure 4C:
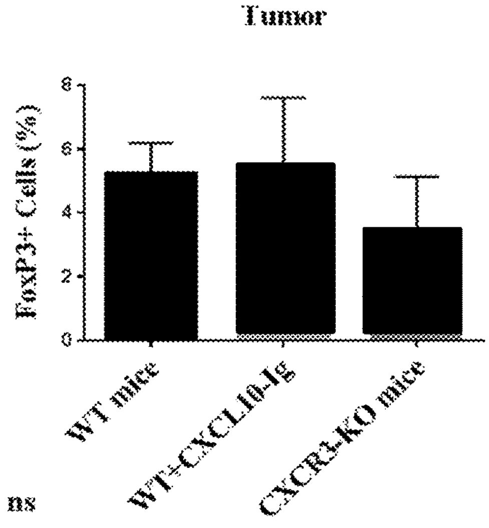
Figure 4D:
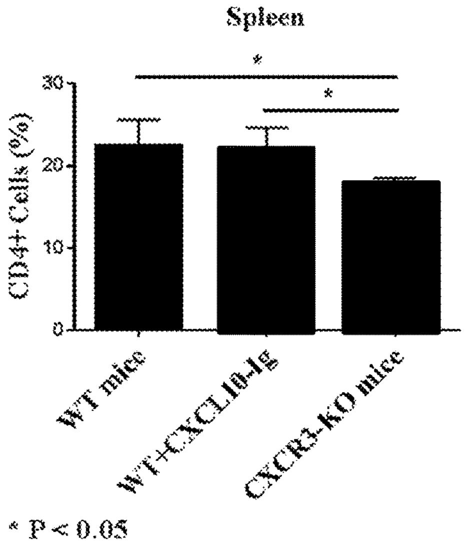
Figure 4E:
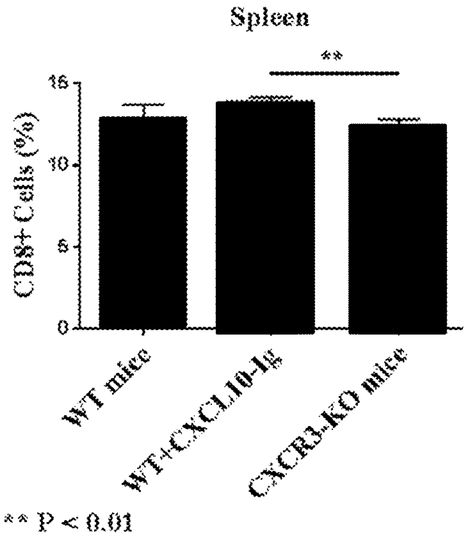
Figure 4F:
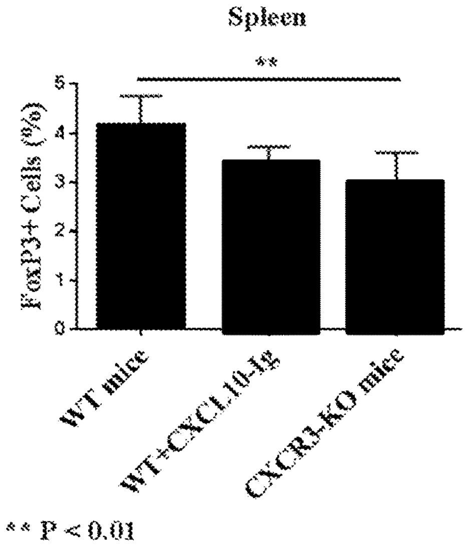

CXCL10-Ig Limits Melanoma Development in Ret Transgenic Mice Transferred Model Via Direct Effect on the Tumor and Tumor Independent Pathways:

At first, the effect of CXCL10-Ig injected to immune-competent mice administered with CXCL10-Ig (treatment beginning when tumor size reached 10 mm$^3$ [7]) in two independent experiments was examined and showed similar results showing marked reduction in tumor volume (FIG. 2, day 35 p<0.001 in each experiment). In the subsequent experiment tumor development in CXCR3KO mice vs WT and CXCR3 mice treated with control IgG vs CXCL10-Ig were compared, as well as WT mice treated with CXCL10-Ig or control IgG. In this experiment tumor assessment included kinetics of tumor development measured by tumor size and tumor weight on day 20. The results clearly show that (1) Administration of CXCL10-Ig has a direct effect on tumor growth when comparing CXCR3 KO mice that were or were not treated with CXCL10-Ig (FIG. 3, P<0.001); (2) a clear tumor independent effect was recorded when comparing WT mice treated with CXCL10-Ig to CXCR3KO mice treated with CXCL10-Ig (FIG. 3, p<0.001). The tumor independent effect may include an effect on CXCR3+ endothelial cells within the tumor site, and immune cells.

Peripheral Administration of CXCL10-Ig Enhances CD8+ T Cell Infiltration to the Tumor Site:

First it was monitored whether peripheral administration of CXCL10-Ig would affect the relative number of infiltrating T cells to the tumor site, and if there is any significant difference in the relative number of these cells in CXCR3KO mice. FIG. 4 shows that administration of CXCL10-Ig led to a significant increase in the relative number of CD8+ T cells at the tumor site (P<0.001). CXCR3KO mice displayed reduced relative number of CD4+ (p<0.05) and CD8+ (p<0.001) T cells. A possible explanation for these data is that administration of CXCL10-Ig potentiates the activity of CD8+ T cells that then home to the tumor site. This possibility was further examined as described below.

Example 3

Figure 5A:
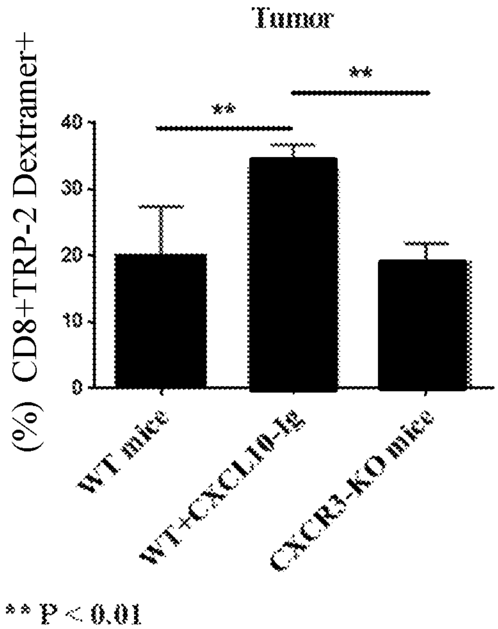
FIGS. 5A-5B show that administration of CXCL10-Ig increased the relative number of tumor specific CD8+ T cell. Ten C57BL/6 (WT) and five CXCR3-KO mice were administered subcutaneous (s.c) with $10^5$ ret melanoma cells. When WT tumors reached size of 2-3 mm, five WT mice were administrated with 10 mg/Kg (about 200 μg/mouse) CXCL10-Ig or isotype matched control IgG twice a week according to their weight, and tumors were harvested at day 21 post tumor challenge. Percentage of TRP2+CD8+ T cells of total CD8+ T cells in the tumor (FIG. 5A) and spleen (FIG. 5B) were analyzed by flow cytometry methods. Results are shown as mean±SD.
Figure 5B:
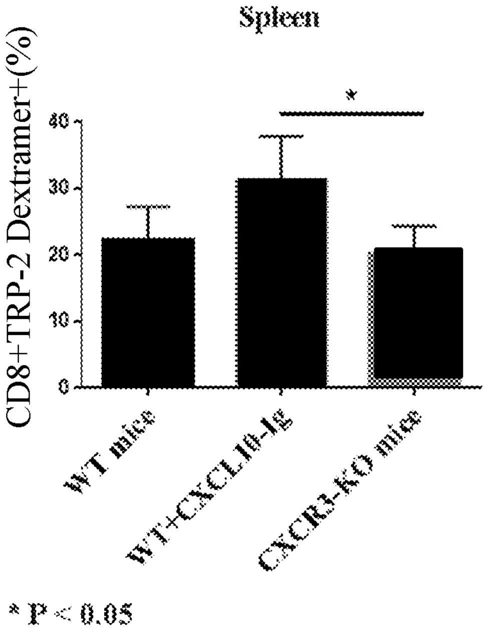
Figure 6A:
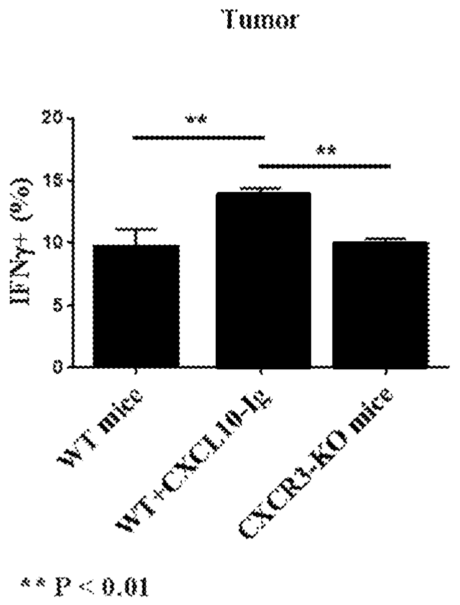
FIGS. 6A-6F show a significant elevation in IFN-γ, Granzyme-B, and TNFa in tumor infiltrating CD8+ T cells following CXCL10-Ig based therapy, and a reduction in these parameters in CXCR3KO mice. Ten C57BL/6 (WT) and five CXCR3-KO mice were administered s.c with $10^5$ ret melanoma cells. When WT tumors reached size of 2-3 mm, five WT mice were administrated with 10 mg/Kg (200 μg/mouse) CXCL10-Ig or isotype matched control IgG, twice a week according to their weight, and tumors were harvested at day 21 post tumor challenge. Percentage of effector and cytotoxic agents: IFNγ, Granzyme B and TNFa in T cells in the tumor (FIGS. 6A, 6B and 6C) and spleen (FIGS. 6D, 6E and 6F) were analyzed in the three groups using standard flow cytometry methods. Results are shown as mean±SD.
Figure 6B:
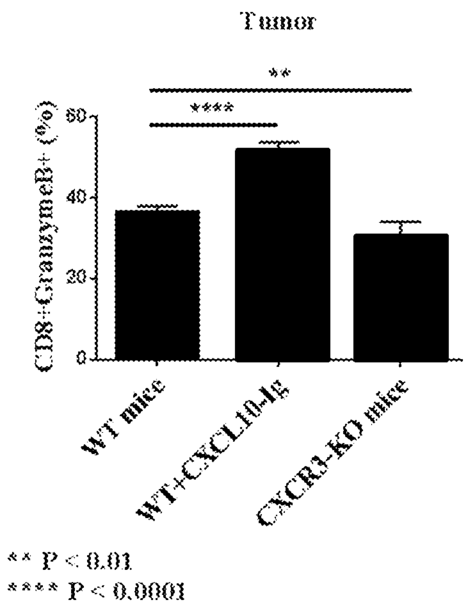
Figure 6C:
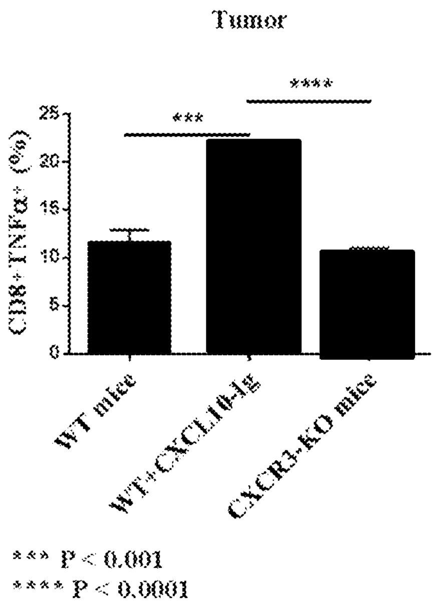
Figure 6D:
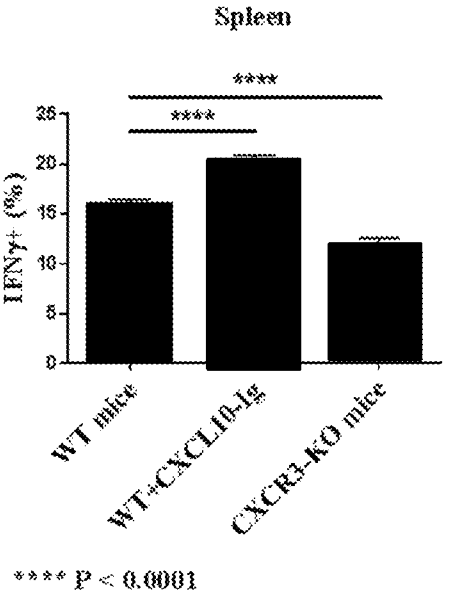
Figure 6E:
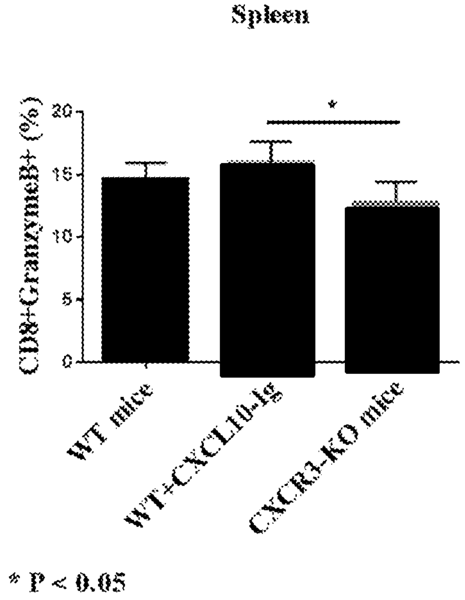
Figure 6F:
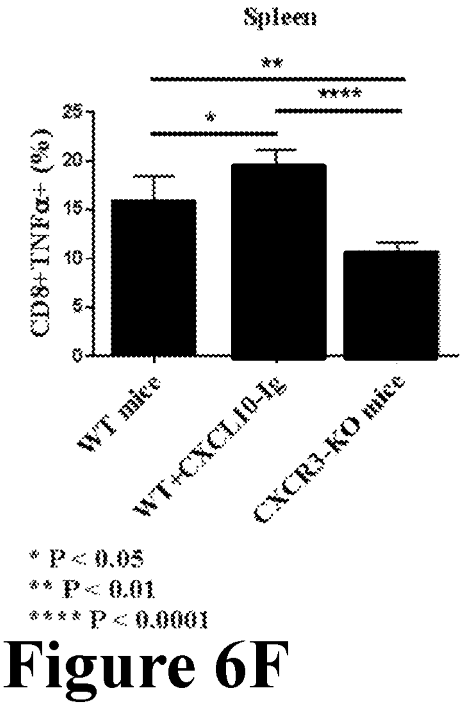

Significant Elevation in the Relative Number of Tumor Specific CD4+ and CD8+ T Cells, and CXCL10-Ig Based Therapy:

Tyrosinase-related protein-2 (TRP-2) is a dominant target antigen for CD4+ and CD8+ T cells in different melanoma murine models, including B16 melanoma, ret transgenic mice, and in C57BL/6 mice engrafted with ret transgenic pre-line. To explore the ability of CXCL10-Ig to induce specific anti-tumor immune responses, WT and CXCR3KO mice were challenged with $10^5$ ret cells. When WT tumors were visible and reached 2-3 mm$^3$ WT mice (five per group) were treated with CXCL10-Ig or control IgG twice a week and the tumors were harvested on day 21. Single cell suspensions were obtained from the tumor and spleen and stained with TRP-2 dextramers specific for CD8+ T cells (Immudex®) and analyzed by flow cytometry. FIG. 5 summarizes data of five different mice per group and shows a significant elevation in the relative number of tumor specific CD8+ T cells at the tumor site following CXCL10-Ig based therapy (about 60% increase in CD8+ T cells, p<0.01). Interestingly, no significant decrease (compared to WT) has been observed in the relative number of these cells in CXCR3KO mice. However, a significant reduction in the activity of tumor infiltrating and spleen CD8+ T cells at the level of IFN-γ, Granzyme-B, and TNF-α in these cells (see FIG. 6).

Example 4 a Significant Elevation in IFN-γ, Granzyme-B, and TNF-α in Tumor Infiltrating CD8+ T Cells Following CXCL10-Ig Based Therapy, and a Reduction in these Parameters in CXCR3KO Mice.

The biological activity of CD8+ effector T cells is associated with higher expression IFN-γ, Granzyme-B and TNF-α. The experimental system described above was used and CD8+ T cells were analyzed by flow cytometry for IFN-γ, Granzyme-B, and TNF-α. FIG. 5 shows the analysis of all 5 mice per group, showing a significant increase in IFN-γ (p<0.01), Granzyme-B (p<0.0001) and TNF-α (p<0.001) in tumor infiltrating CD8+ T cells, and a significant increase in IFN-γ (p<0.0001) and TNF-α (p<0.01) produced by CD8+ T cells. CXCR3KO mice showed reduced Granzyme-B (p<0.01) in tumor infiltrating CD8 cells and of IFN-γ (p<0.0001) and TNF-α (p<0.01) compared to WT.

Example 5

Figure 7A:
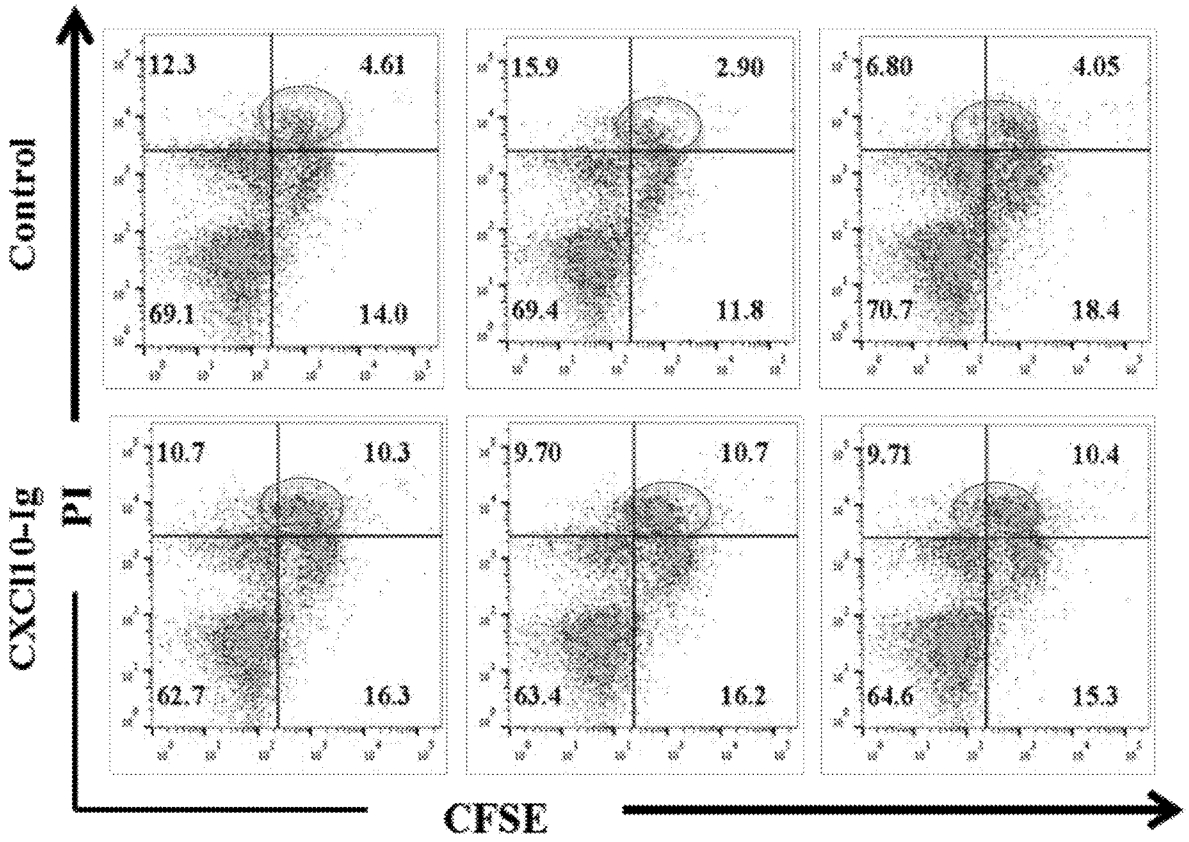
FIGS. 7A and 7B show that administration of CXCL10-Ig (mCXCL10-mIgG-Fc: hinge-CH2-CH3, was used in all examples) increases ex-vivo tumor cell killing by splenic Cytotoxic T lymphocytes (CTLs). CD8+ T cells were separated from spleen of WT control mice, treated with 10 mg/Kg (about 200 μg/mouse) CXCL10-Ig or isotype matched control IgG, and on day 21 post ret challenge CD8+ cells were isolated from the spleen and incubated with CFSE—(Cell-trace labeling dye bind covalently to amines on the surface and inside the cells) labeled ret cells for 24 hours in 10:1 ratio following propidium iodate staining. The samples were analyzed by flow cytometry and dead/live ratio was calculated. Panel 7A shows representative FACS images and panel 7B summarizes mean dead/live ratio of five samples per group. Results are shown as mean±SD.
Figure 7B:
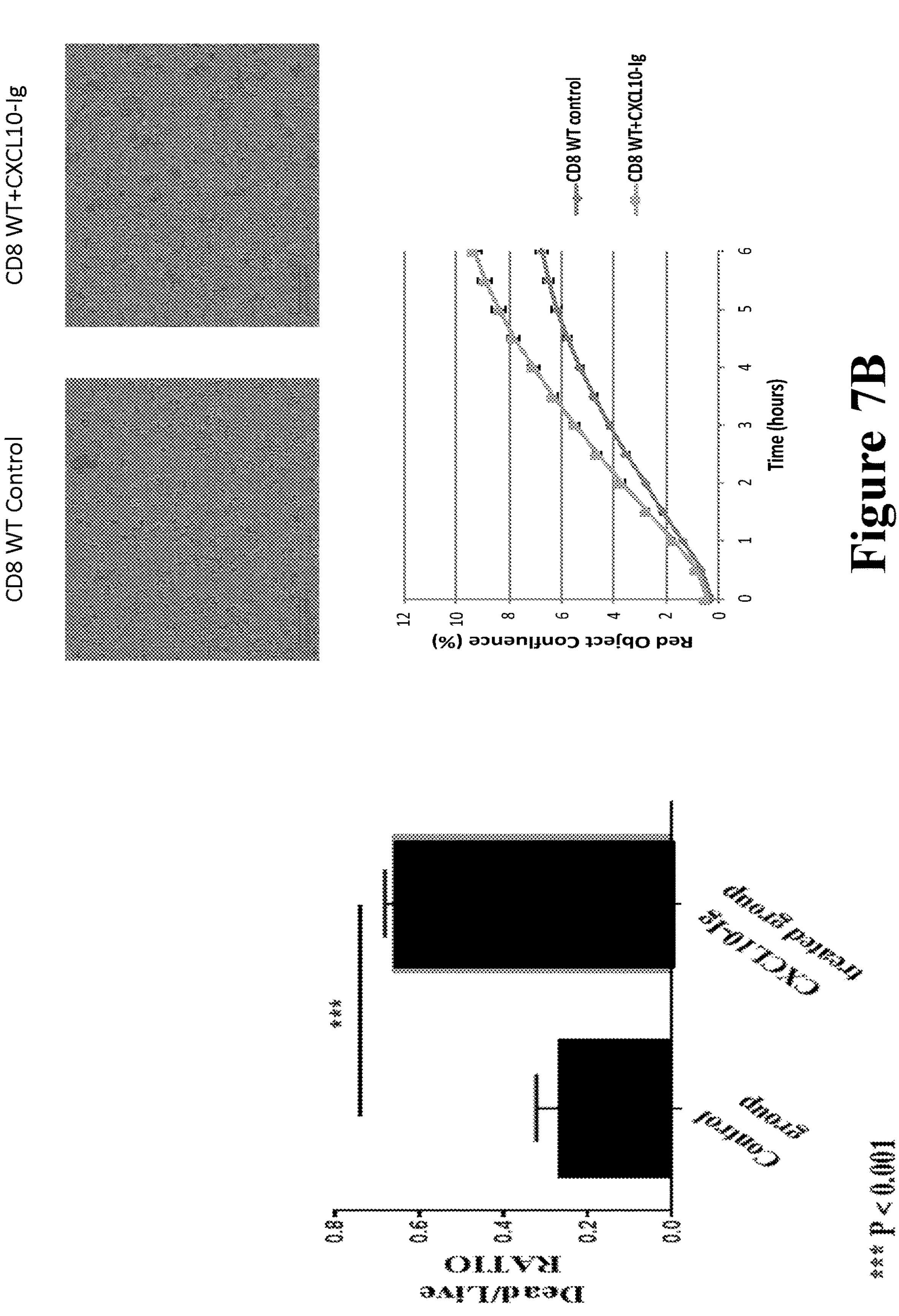

CD8+ T Cells from CXCL10-Ig-Treated Mice Display Augmented Ex-Vivo Cytotoxic Activity Collectively, the results presented above may suggest that CD8+ T cells from CXCL10-Ig-treated mice would display augmented ex-vivo cytotoxic activity. To examine this possibility, CD8+ T cells were isolated from the spleens of WT control and CXCL10-Ig treated WT mice and incubated ex-vivo with ret melanoma cells for 6 hours with PI (dead cells staining marker). FIG. 7A presents representative flow cytometry analysis of three samples from different mice, and FIG. 7B summarizes the mean dead/live cells ratios of samples from 5 mice per group. A higher mean PI fluorescence was observed from 1 to 6 hours after incubation. CXCR3-deficiant CD8+ T cells experienced lower mean PI fluorescence than observed in WT CD8+ T cells (p<0.001). Collectively, the results suggest that, aside of being chemoattractant, CXCL10 potentiates the in vivo activity of tumor specific CD8 T cells.

Example 6

CXCL10-Ig Restrains Melanoma in CXCR3KO Mice Following Reconstitution with CD8+ T Cells from WT but not CXCR3KO Mice To further dissect the direct effect of CXCL10-Ig on the CXCR3+ T cells, CD8+ T cells were isolated from either WT or CXCR3KO mice engrafted with ret melanoma pre-line and transferred to CXCR3KO mice at the same stage of disease (3 days after tumor engraftment). Both recipient groups were treated with CXCL10-Ig (see schematic view on FIG. 7A). The results show that administration of CXCL10-Ig to CXCR3KO mice reconstituted with CXCR3+CD8+ T cells, but not from CXCR3KO lacking reconstitution, suppressed the development of the primary tumor as determined by the kinetics of tumor growth (FIG. 8A, p<0.041), and tumor weight measured on day 20 when the experiment was terminated (FIG. 8B, p<0.0047).

Example 7

Herein three methods by which CXCL10 in its stabilized form (CXCL10-Ig) could be used for effective cancer immunotherapy are presented. The first includes addition of a linker that includes 3 tandem repeats of GGGGS (SEQ ID NO: 7) at the C-terminus site of CXCL10 as a linker between CXCL10 and the Fc (i.e. CXCL10-poly GS). The second protects CXCL10 from DPP4 cleavage, by an insertion of an amino acid at the N-terminus of the CXCL10 to move the position of the Proline from P2 to P3 (positions count from the N-terminus after removing the signal peptide (peptide 1-21)), and thus preventing the cleavage by the aminopeptidase DPP4 that specifically recognizes proline at P2 and cleaves at its C-terminus. Glutamine, asparagine, pyroglutamate or glutamic acid, asparagine or proline may be used as an inserted amino acid at the N-terminus of CXCL10.

Results

Figure 9A:
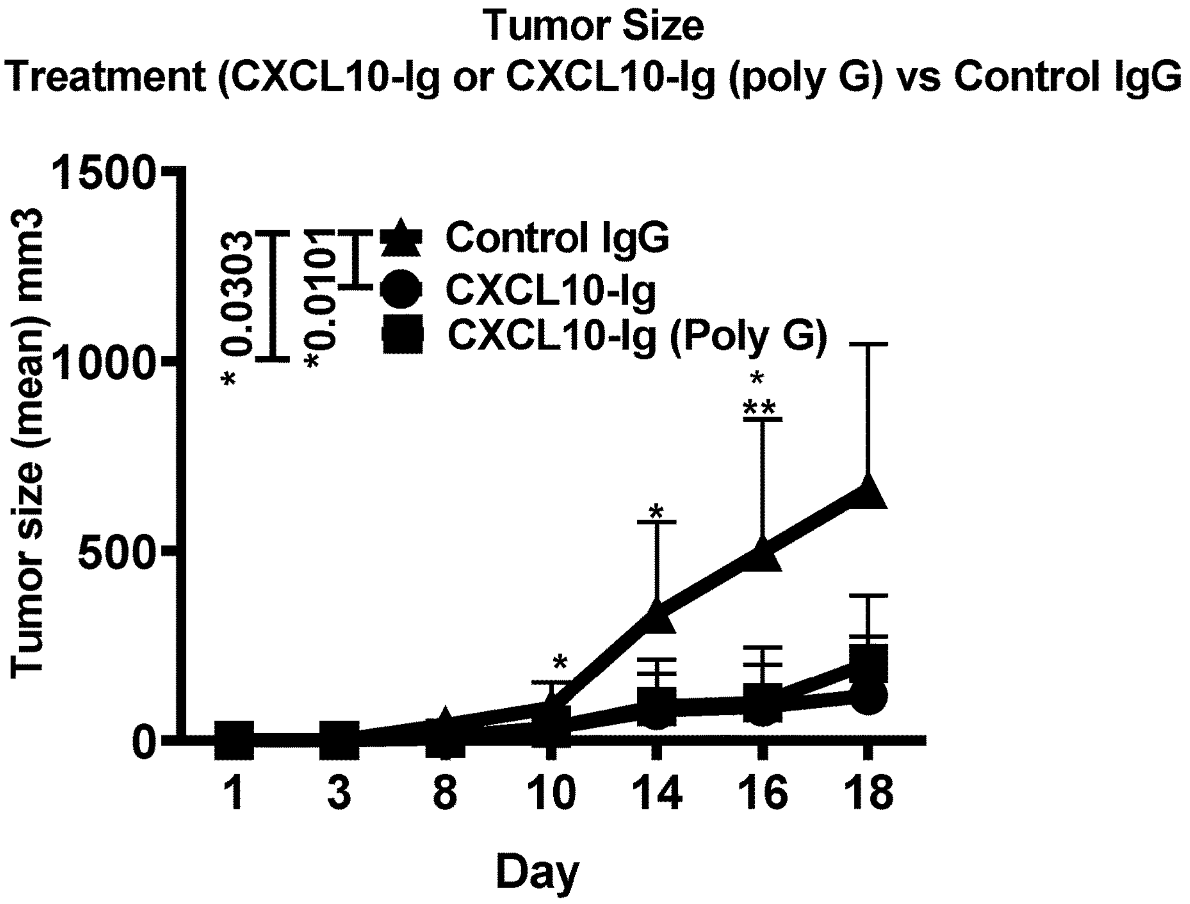
FIGS. 9A and 9B show tumor progression rate in C57Bl/6 mice treated with CXCL10-Ig or CXCL10-Ig (poly GS) in this case, GGGGS in three tandem repeats versus control groups. Mice (21 females at age of 8 weeks) were injected subcutaneously with $3.5\times10^5$ Ret cells at the right side of the bac. On day 3 mice were separated into three groups of seven females each. Group 1 was injected with IgG and serve as negative control. Group 2 was injected with 40 g micrograms of CXCL10-Ig per mouse and Group 3 was injected with 40 micrograms of CXCL10-IgG (Poly GS).
Figure 9B:
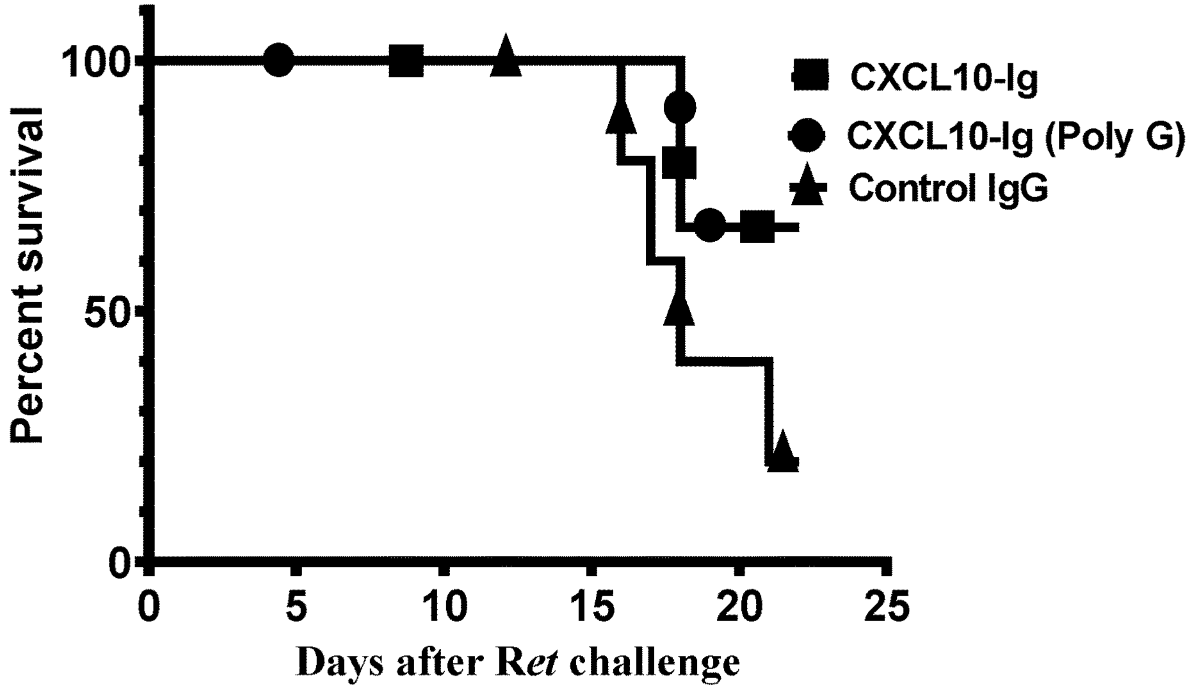
Figure 10A:
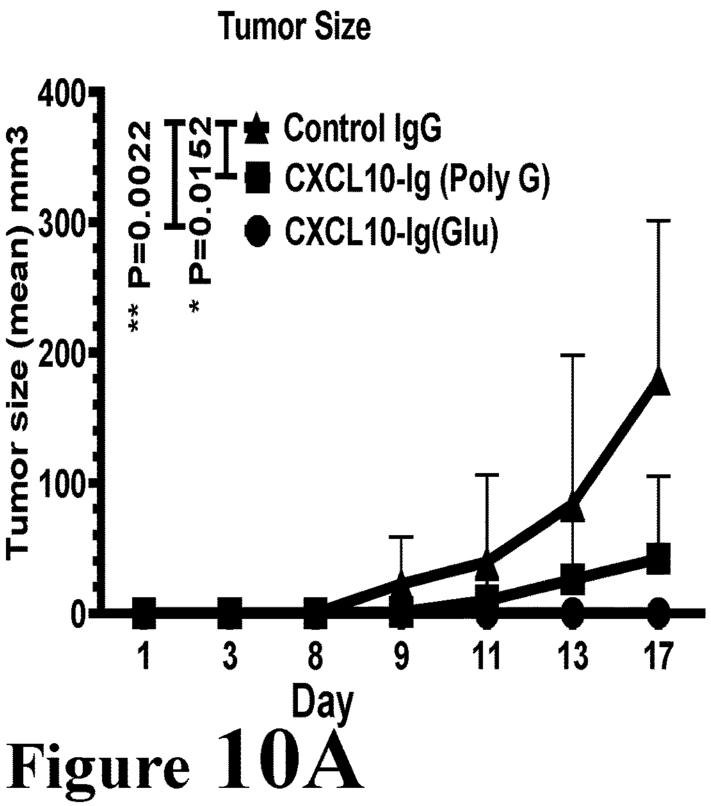
FIGS. 10A-10C show tumor progression rate in C57Bl/6 mice treated with CXCL10-Ig (poly GS) or Gln-CXCL10-Ig. Mice (21 females at age of 8 weeks) were injected subcutaneously with $3.5\times10^5$ Ret cells at the back. On day 3 mice were separated into 3 groups of 6-7 females each. Each group was treated (3 time a week, 40 μg/mouse) with either CXCL10-Ig (poly GS), in this case, GGGGS in 3 tandem repeats, or Gln-CXCL10-Ig i.e. CXCL10 with IgG-Fc having an additional glutamine at the N-terminus, or with isotype matched control IgG (calibrated according molar adjustment). On day 9 a single mouse in the control group that developed a significantly enlarged tumor compared to all other mice in the same group has been excluded from the experiment. Subsequently the number of mice in the other groups has been adjusted accordingly (6 mice per group). On day 23 therapy was terminated and mice were continued to be followed for mortality.

FIG. 9 shows the results of an experiment in which the ability of CXCL10-Ig with (poly GS) (as in SEQ ID No: 6) and CXCL10-Ig without this addition (i.e CXCL10-Ig) to inhibit experimental melanoma. FIG. 10A follows tumor development and FIG. 10B follows mortality (Kaplan Meier plot). Both indicate that the addition of poly GS to the linker maintains but not improves the ability of CXCL10-Ig to restrain tumor development.

Figure 10B:
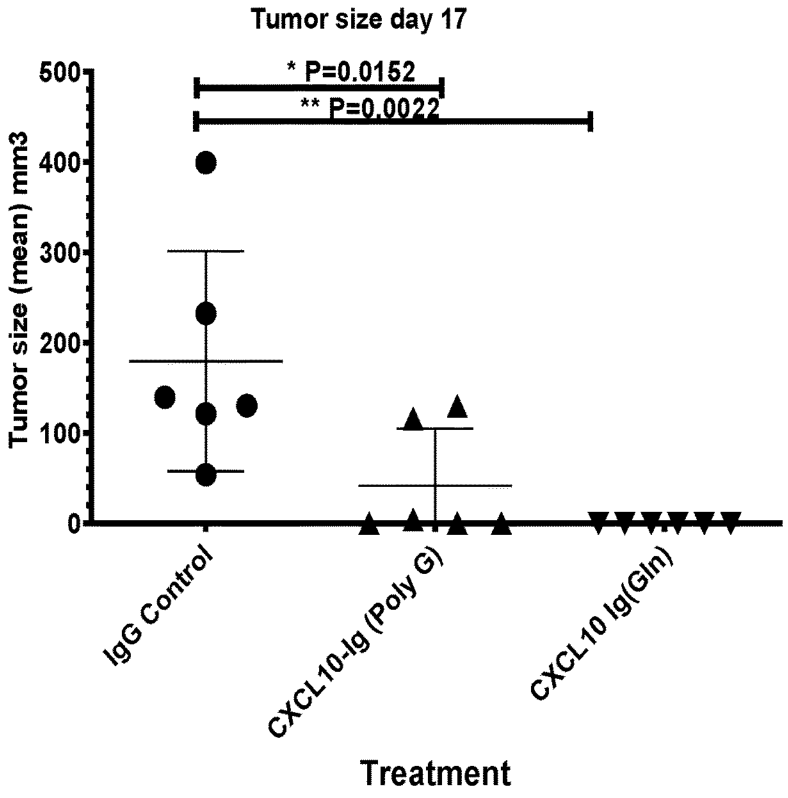
Figure 10C:
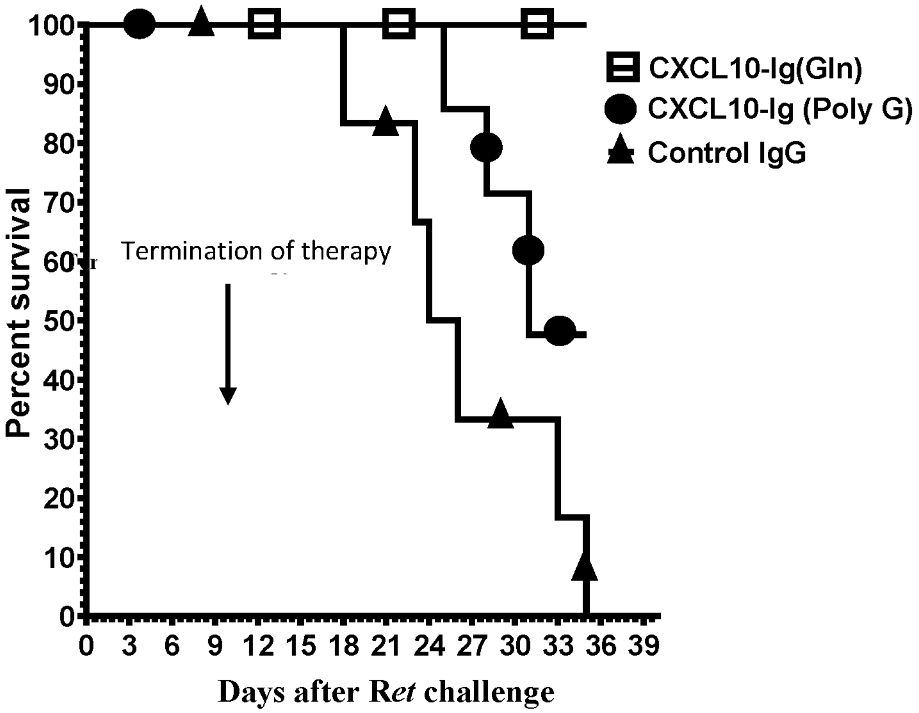

FIG. 10 shows the results of an experiment in which the ability of CXCL10-Ig (Gln) with an additional Glutamine at the N-terminus site, and CXCL10-Ig without this addition (i.e CXCL10-Ig, as explained above the Ig is IgG-Fc: hinge-ch2-ch3) to inhibit experimental melanoma were compared. FIGS. 10A-10B follow tumor development and FIG. 10C follows mortality (Kaplan Meier plot). Altogether they clearly show that modified CXCL10-Ig with an addition of Gln significantly inhibits tumor growth (panel A & B) and totally prevent mortality (0/6 compared to 3/6 in CXCL10-Ig treated mice, and 6/6 in control mice). Thus, addition of Gln (and also of Asn or Pro at the N-terminus site of CXCL10) would enhance its anti-cancer properties. The results clearly show that addition of Gln to the N-terminus site of the chemokine to protect it from DPP4 cleavage markedly enhances the ability of CXCL10-Ig to suppress cancer development.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is to be understood that further trials are being conducted to establish clinical effects.

What is claimed is:

1. A method of treating cancer melanoma in a subject in need thereof, the method comprising administering to the subject a therapeutically effective amount of a pharmaceutical composition comprising a modified CXCL10 polypeptide, wherein the modified CXCL10 polypeptide has been modified by an addition of a glutamine amino acid to an N-terminus thereof following removal of a signal peptide consisting of amino acids at positions 1-21 of the CXCL10 polypeptide.

2. The method of claim 1, wherein the modified CXCL10 polypeptide is linked to an immunoglobulin (Ig) molecule or a fragment of an Ig molecule.

3. The method of claim 2, wherein the modified CXCL10 polypeptide further comprises a linker between the modified CXCL10 and the Ig molecule or the fragment thereof.

4. The method of claim 2, wherein the Ig or the fragment thereof is of a human origin.

5. The method of claim 1, wherein the modified CXCL10 polypeptide is linked to an IgG-Fc: hingeCH2CH3 fragment defined denoted by SEQ ID NO: 5.

6. The method of claim 1, wherein the modified CXCL10 polypeptide is capable of binding to a CXCR3 receptor and/or inducing CD8+ T cells.

* * * * *

SEQUENCE LISTING

```
Sequence total quantity: 49
SEQ ID NO: 1          moltype = AA  length = 99
FEATURE               Location/Qualifiers
REGION                1..99
                      note = Synthetic Sequence
VARIANT               22
                      note = Xaa can be any naturally occurring amino acid
source                1..99
                      mol_type = protein
                      organism = synthetic construct
SEQUENCE: 1
MNQTAILICC LIFLTLSGIQ GXVPLSRTVR CTCISISNQP VNPRSLEKLE IIPASQFCPR  60
VEIIATMKKK GEKRCLNPES KAIKNLLKAV SKERSKRSP                         99

SEQ ID NO: 2          moltype = AA  length = 99
FEATURE               Location/Qualifiers
REGION                1..99
                      note = Synthetic Sequence
source                1..99
                      mol_type = protein
                      organism = synthetic construct
SEQUENCE: 2
MNQTAILICC LIFLTLSGIQ GQVPLSRTVR CTCISISNQP VNPRSLEKLE IIPASQFCPR  60
VEIIATMKKK GEKRCLNPES KAIKNLLKAV SKERSKRSP                         99

SEQ ID NO: 3          moltype = AA  length = 99
FEATURE               Location/Qualifiers
REGION                1..99
                      note = Synthetic Sequence
source                1..99
                      mol_type = protein
                      organism = synthetic construct
SEQUENCE: 3
```

```
MNQTAILICC LIFLTLSGIQ GNVPLSRTVR CTCISISNQP VNPRSLEKLE IIPASQFCPR  60
VEIIATMKKK GEKRCLNPES KAIKNLLKAV SKERSKRSP                         99

SEQ ID NO: 4            moltype = AA  length = 99
FEATURE                 Location/Qualifiers
REGION                  1..99
                        note = Synthetic Sequence
source                  1..99
                        mol_type = protein
                        organism = synthetic construct
SEQUENCE: 4
MNQTAILICC LIFLTLSGIQ GPVPLSRTVR CTCISISNQP VNPRSLEKLE IIPASQFCPR  60
VEIIATMKKK GEKRCLNPES KAIKNLLKAV SKERSKRSP                         99

SEQ ID NO: 5            moltype = AA  length = 232
FEATURE                 Location/Qualifiers
REGION                  1..232
                        note = Synthetic Sequence
source                  1..232
                        mol_type = protein
                        organism = synthetic construct
SEQUENCE: 5
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 6            moltype = DNA  length = 15
FEATURE                 Location/Qualifiers
misc_feature            1..15
                        note = Synthetic Sequence
source                  1..15
                        mol_type = other DNA
                        organism = synthetic construct
SEQUENCE: 6
ggggsggggs ggggs                                                   15

SEQ ID NO: 7            moltype =   length =
SEQUENCE: 7
000

SEQ ID NO: 8            moltype = AA  length = 98
FEATURE                 Location/Qualifiers
REGION                  1..98
                        note = Synthetic Sequence
source                  1..98
                        mol_type = protein
                        organism = synthetic construct
SEQUENCE: 8
MNQTAILICC LIFLTLSGIQ GVPLSRTVRC TCISISNQPV NPRSLEKLEI IPASQFCPRV  60
EIIATMKKKG EKRCLNPESK AIKNLLKAVS KERSKRSP                          98

SEQ ID NO: 9            moltype = DNA  length = 294
FEATURE                 Location/Qualifiers
misc_feature            1..294
                        note = Synthetic Sequence
source                  1..294
                        mol_type = other DNA
                        organism = synthetic construct
SEQUENCE: 9
atgaatcaaa ctgccattct gatttgctgc cttatctttc tgactctaag tggcattcaa  60
ggagtacctc tctctagaac tgtacgctgt acctgcatca gcattagtaa tcaacctgtt  120
aatccaaggt ctttagaaaa acttgaaatt attcctgcaa gccaattttg tccacgtgtt  180
gagatcattg ctacaatgaa aaagaagggt gagaagagat gtctgaatcc agaatcgaag  240
gccatcaaga atttactgaa agcagttagc aaggaaaggt ctaaaagatc tcct        294

SEQ ID NO: 10           moltype = DNA  length = 297
FEATURE                 Location/Qualifiers
misc_feature            1..297
                        note = Synthetic Sequence
source                  1..297
                        mol_type = other DNA
                        organism = synthetic construct
SEQUENCE: 10
atgaatcaaa ctgccattct gatttgctgc cttatctttc tgactctaag tggcattcaa  60
ggacaagtac ctctctctag aactgtacgc tgtacctgca tcagcattag taatcaacct  120
gttaatccaa ggtctttaga aaaacttgaa attattcctg caagccaatt ttgtccacgt  180
gttgagatca ttgctacaat gaaaaagaag ggtgagaaga gatgtctgaa tccagaatcg  240
aaggccatca agaatttact gaaagcagtt agcaaggaaa ggtctaaaag atctcct     297
```

```
SEQ ID NO: 11          moltype = DNA  length = 297
FEATURE                Location/Qualifiers
misc_feature           1..297
                       note = Synthetic Sequence
source                 1..297
                       mol_type = other DNA
                       organism = synthetic construct
SEQUENCE: 11
atgaatcaaa ctgccattct gatttgctgc cttatctttc tgactctaag tggcattcaa  60
ggaaacgtac ctctctctag aactgtacgc tgtacctgca tcagcattag taatcaacct  120
gttaatccaa ggtctttaga aaaacttgaa attattcctg caagccaatt ttgtccacgt  180
gttgagatca ttgctacaat gaaaaagaag ggtgagaaga gatgtctgaa tccagaatcg  240
aaggccatca agaatttact gaaagcagtt agcaaggaaa ggtctaaaag atctcct     297

SEQ ID NO: 12          moltype = DNA  length = 297
FEATURE                Location/Qualifiers
misc_feature           1..297
                       note = Synthetic Sequence
source                 1..297
                       mol_type = other DNA
                       organism = synthetic construct
SEQUENCE: 12
atgaatcaaa ctgccattct gatttgctgc cttatctttc tgactctaag tggcattcaa  60
ggacccgtac ctctctctag aactgtacgc tgtacctgca tcagcattag taatcaacct  120
gttaatccaa ggtctttaga aaaacttgaa attattcctg caagccaatt ttgtccacgt  180
gttgagatca ttgctacaat gaaaaagaag ggtgagaaga gatgtctgaa tccagaatcg  240
aaggccatca agaatttact gaaagcagtt agcaaggaaa ggtctaaaag atctcct     297

SEQ ID NO: 13          moltype = DNA  length = 696
FEATURE                Location/Qualifiers
misc_feature           1..696
                       note = Synthetic Sequence
source                 1..696
                       mol_type = other DNA
                       organism = synthetic construct
SEQUENCE: 13
gagcccaaat cttgtgacaa aactcacaca tgcccaccgt gcccagcacc tgaactcctg  60
gggggaccgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcccccat cgagaaaacc  360
atctccaaag ccaaagggca gccccgagaa ccacaggtgt acaccctgcc cccatcccgg  420
gaggagatga ccaagaacca ggtcagcctg acctgcctgg tcaaaggctt ctatcccagc  480
gacatcgccg tggagtggga gagcaatggg cagccggaga acaactacaa gaccacgcct  540
cccgtgctgg actccgacgg ctccttcttc ctctatagca agctcaccgt ggacaagagc  600
aggtggcagc aggggaacgt cttctcatgc tccgtgatgc atgaggctct gcacaaccac  660
tacacgcaga agagcctctc cctgtccccg ggtaaa                            696

SEQ ID NO: 14          moltype = AA  length = 98
FEATURE                Location/Qualifiers
REGION                 1..98
                       note = Synthetic Sequence
source                 1..98
                       mol_type = protein
                       organism = synthetic construct
SEQUENCE: 14
MNQTAILICC LIFLTLSGIQ GVPLSKTVRC TCISISNQPV NPRSLEKLEI IPASQFCPRV  60
EIIATMKKKG EKRCLNPESK AIKNLLKAVS KERSKRSP                          98

SEQ ID NO: 15          moltype = AA  length = 98
FEATURE                Location/Qualifiers
REGION                 1..98
                       note = Synthetic Sequence
source                 1..98
                       mol_type = protein
                       organism = synthetic construct
SEQUENCE: 15
MNQTAILICC LIFLTLSGIQ GVPLSHTVRC TCISISNQPV NPRSLEKLEI IPASQFCPRV  60
EIIATMKKKG EKRCLNPESK AIKNLLKAVS KERSKRSP                          98

SEQ ID NO: 16          moltype = DNA  length = 294
FEATURE                Location/Qualifiers
misc_feature           1..294
                       note = Synthetic Sequence
source                 1..294
                       mol_type = other DNA
                       organism = synthetic construct
```

```
SEQUENCE: 16
atgaatcaaa ctgccattct gatttgctgc cttatctttc tgactctaag tggcattcaa  60
ggagtacctc tctctcacac tgtacgctgt acctgcatca gcattagtaa tcaacctgtt  120
aatccaaggt ctttagaaaa acttgaaatt attcctgcaa gccaattttg tccacgtgtt  180
gagatcattg ctacaatgaa aaagaagggt gagaagagat gtctgaatcc agaatcgaag  240
gccatcaaga atttactgaa agcagttagc aaggaaaggt ctaaaagatc tcct        294

SEQ ID NO: 17           moltype = DNA  length = 294
FEATURE                 Location/Qualifiers
misc_feature            1..294
                        note = Synthetic Sequence
source                  1..294
                        mol_type = other DNA
                        organism = synthetic construct
SEQUENCE: 17
atgaatcaaa ctgccattct gatttgctgc cttatctttc tgactctaag tggcattcaa  60
ggagtacctc tctctaagac tgtacgctgt acctgcatca gcattagtaa tcaacctgtt  120
aatccaaggt ctttagaaaa acttgaaatt attcctgcaa gccaattttg tccacgtgtt  180
gagatcattg ctacaatgaa aaagaagggt gagaagagat gtctgaatcc agaatcgaag  240
gccatcaaga atttactgaa agcagttagc aaggaaaggt ctaaaagatc tcct        294

SEQ ID NO: 18           moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 18
MNQTAILICC LIFLTLSGIQ GVPLSRTVRC TCISISNQPV NPRSLEKLEI IPASQFCPRV  60
EIIATMKKKG EKRCLNPESK AIKNLLKAVS KERSKRSPGG GGSGGGGSGG GGS         113

SEQ ID NO: 19           moltype = DNA  length = 339
FEATURE                 Location/Qualifiers
misc_feature            1..339
                        note = Synthetic Sequence
source                  1..339
                        mol_type = other DNA
                        organism = synthetic construct
SEQUENCE: 19
atgaatcaaa ctgccattct gatttgctgc cttatctttc tgactctaag tggcattcaa  60
ggagtacctc tctctagaac tgtacgctgt acctgcatca gcattagtaa tcaacctgtt  120
aatccaaggt ctttagaaaa acttgaaatt attcctgcaa gccaattttg tccacgtgtt  180
gagatcattg ctacaatgaa aaagaagggt gagaagagat gtctgaatcc agaatcgaag  240
gccatcaaga atttactgaa agcagttagc aaggaaaggt ctaaaagatc tcctggcgga  300
ggtggctctg gcggtggcgg atcgggcgga ggtggctct                         339

SEQ ID NO: 20           moltype = AA  length = 98
FEATURE                 Location/Qualifiers
REGION                  1..98
                        note = Synthetic Sequence
source                  1..98
                        mol_type = protein
                        organism = synthetic construct
SEQUENCE: 20
MNPSAAVIFC LILLGLSGTQ GIPLARTVRC NCIHIDDGPV RMRAIGKLEI IPASLSCPRV  60
EIIATMKKND EQRCLNPESK TIKNLMKAFS QKRSKRAP                          98

SEQ ID NO: 21           moltype = AA  length = 227
FEATURE                 Location/Qualifiers
REGION                  1..227
                        note = Synthetic Sequence
source                  1..227
                        mol_type = protein
                        organism = synthetic construct
SEQUENCE: 21
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDCLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGK                227

SEQ ID NO: 22           moltype = AA  length = 98
FEATURE                 Location/Qualifiers
REGION                  1..98
                        note = Synthetic Sequence
source                  1..98
                        mol_type = protein
                        organism = synthetic construct
SEQUENCE: 22
```

```
MNPSAAVIFC LILLGLSGTQ GIPLAHTVRC NCIHIDDGPV RMRAIGKLEI IPASLSCPRV  60
EIIATMKKND EQRCLNPESK TIKNLMKAFS QKRSKRAP                          98

SEQ ID NO: 23          moltype = AA  length = 98
FEATURE                Location/Qualifiers
REGION                 1..98
                       note = Synthetic Sequence
source                 1..98
                       mol_type = protein
                       organism = synthetic construct
SEQUENCE: 23
MNPSAAVIFC LILLGLSGTQ GIPLAKTVRC NCIHIDDGPV RMRAIGKLEI IPASLSCPRV  60
EIIATMKKND EQRCLNPESK TIKNLMKAFS QKRSKRAP                          98

SEQ ID NO: 24          moltype = AA  length = 99
FEATURE                Location/Qualifiers
REGION                 1..99
                       note = Synthetic Sequence
source                 1..99
                       mol_type = protein
                       organism = synthetic construct
SEQUENCE: 24
MNPSAAVIFC LILLGLSGTQ GQIPLARTVR CNCIHIDDGP VRMRAIGKLE IIPASLSCPR  60
VEIIATMKKN DEQRCLNPES KTIKNLMKAF SQKRSKRAP                         99

SEQ ID NO: 25          moltype = AA  length = 113
FEATURE                Location/Qualifiers
REGION                 1..113
                       note = Synthetic Sequence
source                 1..113
                       mol_type = protein
                       organism = synthetic construct
SEQUENCE: 25
MNPSAAVIFC LILLGLSGTQ GIPLARTVRC NCIHIDDGPV RMRAIGKLEI IPASLSCPRV  60
EIIATMKKND EQRCLNPESK TIKNLMKAFS QKRSKRAPGG GGSGGGGSGG GGS         113

SEQ ID NO: 26          moltype = DNA  length = 339
FEATURE                Location/Qualifiers
misc_feature           1..339
                       note = Synthetic Sequence
source                 1..339
                       mol_type = other DNA
                       organism = synthetic construct
SEQUENCE: 26
atgaacccaa gtgctgccgt cattttctgc ctcatcctgc tgggtctgag tgggactcaa  60
gggatccctc tcgcaaggac ggtccgctgc aactgcatcc atatcgatga cgggccagtg  120
agaatgaggg ccatagggaa gcttgaaatc atccctgcga gcctatcctg cccacgtgtt  180
gagatcattg ccacgatgaa aaagaatgat gagcagagat gtctgaatcc ggaatctaag  240
accatcaaga atttaatgaa agcgtttagc caaaaaaggt ctaaaagggc tcctggcgga  300
ggtggctctg gcggtggcgg atcgggcgga ggtggctct                         339

SEQ ID NO: 27          moltype = DNA  length = 298
FEATURE                Location/Qualifiers
misc_feature           1..298
                       note = Synthetic Sequence
source                 1..298
                       mol_type = other DNA
                       organism = synthetic construct
SEQUENCE: 27
atgaacccaa gtgctgccgt cattttctgc ctcatcctgc tgggtctgag tgggactcaa  60
gggcaaatcc ctctcgcaag gacggtccgc tgcaactgca tccatatcga tgacgggcca  120
gtgagaatga gggccatagg gaagcttgaa atcatccctg cgagcctatc ctgcccacgt  180
gttgagatca ttgccacgat gaaaaagaat gatgagcaga gatgtctgaa tccggaatct  240
aagaccatca agaatttaat gaaagcgttt agccaaaaaa ggtctaaaag ggctcctc    298

SEQ ID NO: 28          moltype = AA  length = 326
FEATURE                Location/Qualifiers
REGION                 1..326
                       note = Synthetic Sequence
source                 1..326
                       mol_type = protein
                       organism = synthetic construct
SEQUENCE: 28
MNQTAILICC LIFLTLSGIQ GQVPLSRTVR CTCISISNQP VNPRSLEKLE IIPASQFCPR  60
VEIIATMKKK GEKRCLNPES KAIKNLLKAV SKERSKRSPV PRDCGCKPCI CTVPEVSSVF  120
IFPPKPKDVL TITLTPKVTC VVVDISKDDP EVQFSWFVDD VEVHTAQTQP REEQFNSTFR  180
SVSELPIMHQ DCLNGKEFKC RVNSAAFPAP IEKTISKTKG RPKAPQVYTI PPPKEQMAKD  240
KVSLTCMITD FFPEDITVEW QWNGQPAENY KNTQPIMDTD GSYFVYSKLN VQKSNWEAGN  300
TFTCSVLHEG LHNHHTEKSL SHSPGK                                       326
```

```
SEQ ID NO: 29          moltype = DNA  length = 978
FEATURE                Location/Qualifiers
misc_feature           1..978
                       note = Synthetic Sequence
source                 1..978
                       mol_type = other DNA
                       organism = synthetic construct
SEQUENCE: 29
atgaatcaaa ctgccattct gatttgctgc cttatctttc tgactctaag tggcattcaa  60
ggacaagtac ctctctctag aactgtacgc tgtacctgca tcagcattag taatcaacct  120
gttaatccaa ggtctttaga aaaacttgaa attattcctg caagccaatt ttgtccacgt  180
gttgagatca ttgctacaat gaaaaagaag ggtgagaaga gatgtctgaa tccagaatcg  240
aaggccatca agaatttact gaaagcagtt agcaaggaaa ggtctaaaag atctcctgtg  300
cccagggatt gtggttgtaa gccttgcata tgtacagtcc cagaagtatc atctgtcttc  360
atcttccccc caaagcccaa ggatgtgctc accattactc tgactcctaa ggtcacgtgt  420
gttgtggtag acatcagcaa ggatgatccc gaggtccagt tcagctggtt tgtagatgat  480
gtggaggtgc acacagctca gacgcaaccc cgggaggagc agttcaacag cactttccgc  540
tcagtcagtg aacttcccat catgcaccag gactgcctca atggcaagga gttcaaatgc  600
agggtcaaca gtgcagcttt ccctgccccc atcgagaaaa ccatctccaa aaccaaaggc  660
agaccgaagg ctccacaggt gtacaccatt ccacctccca aggagcagat ggccaaggat  720
aaagtcagtc tgacctgcat gataacagac ttcttccctg aagacattac tgtggagtgg  780
cagtggaatg ggcagccagc ggagaactac aagaacactc agcccatcat ggacacagat  840
ggctcttact tcgtctacag caagctcaat gtgcagaaga gcaactggga ggcaggaaat  900
actttcacct gctctgtgtt acatgagggc ctgcacaacc accatactga gaagagcctc  960
tcccactctc ctggtaaa                                                978

SEQ ID NO: 30          moltype = AA  length = 326
FEATURE                Location/Qualifiers
REGION                 1..326
                       note = Synthetic Sequence
source                 1..326
                       mol_type = protein
                       organism = synthetic construct
SEQUENCE: 30
MNQTAILICC LIFLTLSGIQ GNVPLSRTVR CTCISISNQP VNPRSLEKLE IIPASQFCPR  60
VEIIATMKKK GEKRCLNPES KAIKNLLKAV SKERSKRSPV PRDCGCKPCI CTVPEVSSVF  120
IFPPKPKDVL TITLTPKVTC VVVDISKDDP EVQFSWFVDD VEVHTAQTQP REEQFNSTFR  180
SVSELPIMHQ DCLNGKEFKC RVNSAAFPAP IEKTISKTKG RPKAPQVYTI PPPKEQMAKD  240
KVSLTCMITD FFPEDITVEW QWNGQPAENY KNTQPIMDTD GSYFVYSKLN VQKSNWEAGN  300
TFTCSVLHEG LHNHHTEKSL SHSPGK                                       326

SEQ ID NO: 31          moltype = DNA  length = 978
FEATURE                Location/Qualifiers
misc_feature           1..978
                       note = Synthetic Sequence
source                 1..978
                       mol_type = other DNA
                       organism = synthetic construct
SEQUENCE: 31
atgaatcaaa ctgccattct gatttgctgc cttatctttc tgactctaag tggcattcaa  60
ggaaatgtac ctctctctag aactgtacgc tgtacctgca tcagcattag taatcaacct  120
gttaatccaa ggtctttaga aaaacttgaa attattcctg caagccaatt ttgtccacgt  180
gttgagatca ttgctacaat gaaaaagaag ggtgagaaga gatgtctgaa tccagaatcg  240
aaggccatca agaatttact gaaagcagtt agcaaggaaa ggtctaaaag atctcctgtg  300
cccagggatt gtggttgtaa gccttgcata tgtacagtcc cagaagtatc atctgtcttc  360
atcttccccc caaagcccaa ggatgtgctc accattactc tgactcctaa ggtcacgtgt  420
gttgtggtag acatcagcaa ggatgatccc gaggtccagt tcagctggtt tgtagatgat  480
gtggaggtgc acacagctca gacgcaaccc cgggaggagc agttcaacag cactttccgc  540
tcagtcagtg aacttcccat catgcaccag gactgcctca atggcaagga gttcaaatgc  600
agggtcaaca gtgcagcttt ccctgccccc atcgagaaaa ccatctccaa aaccaaaggc  660
agaccgaagg ctccacaggt gtacaccatt ccacctccca aggagcagat ggccaaggat  720
aaagtcagtc tgacctgcat gataacagac ttcttccctg aagacattac tgtggagtgg  780
cagtggaatg ggcagccagc ggagaactac aagaacactc agcccatcat ggacacagat  840
ggctcttact tcgtctacag caagctcaat gtgcagaaga gcaactggga ggcaggaaat  900
actttcacct gctctgtgtt acatgagggc ctgcacaacc accatactga gaagagcctc  960
tcccactctc ctggtaaa                                                978

SEQ ID NO: 32          moltype = AA  length = 340
FEATURE                Location/Qualifiers
REGION                 1..340
                       note = Synthetic Sequence
source                 1..340
                       mol_type = protein
                       organism = synthetic construct
SEQUENCE: 32
MNQTAILICC LIFLTLSGIQ GVPLSRTVRC TCISISNQPV NPRSLEKLEI IPASQFCPRV  60
EIIATMKKKG EKRCLNPESK AIKNLLKAVS KERSKRSPGG GGSGGGGSGG GGSVPRDCGC  120
KPCICTVPEV SSVFIFPPKP KDVLTITLTP KVTCVVVDIS KDDPEVQFSW FVDDVEVHTA  180
```

```
QTQPREEQFN STFRSVSELP IMHQDCLNGK EFKCRVNSAA FPAPIEKTIS KTKGRPKAPQ  240
VYTIPPPKEQ MAKDKVSLTC MITDFFPEDI TVEWQWNGQP AENYKNTQPI MDTDGSYFVY  300
SKLNVQKSNW EAGNTFTCSV LHEGLHNHHT EKSLSHSPGK                        340

SEQ ID NO: 33          moltype = DNA  length = 1020
FEATURE                Location/Qualifiers
misc_feature           1..1020
                       note = Synthetic Sequence
source                 1..1020
                       mol_type = other DNA
                       organism = synthetic construct
SEQUENCE: 33
atgaatcaaa ctgccattct gatttgctgc cttatctttc tgactctaag tggcattcaa  60
ggagtacctc tctctagaac tgtacgctgt acctgcatca gcattagtaa tcaacctgtt  120
aatccaaggt ctttagaaaa acttgaaatt attcctgcaa gccaattttg tccacgtgtt  180
gagatcattg ctacaatgaa aaagaagggt gagaagagat gtctgaatcc agaatcgaag  240
gccatcaaga atttactgaa agcagttagc aaggaaaggt ctaaaagatc tcctggcgga  300
ggtggctctg gcggtggcgg atcgggcgga ggtggctctg tgcccaggga ttgtggttgt  360
aagccttgca tatgtacagt cccagaagta tcatctgtct tcatcttccc cccaaagccc  420
aaggatgtgc tcaccattac tctgactcct aaggtcacgt gtgttgtggt agacatcagc  480
aaggatgatc ccgaggtcca gttcagctgg tttgtagatg atgtggaggt gcacacagct  540
cagacgcaac cccgggagga gcagttcaac agcactttcc gctcagtcag tgaacttccc  600
atcatgcacc aggactgcct caatggcaag gagttcaaat gcagggtcaa cagtgcagct  660
ttccctgccc ccatcgagaa aaccatctcc aaaaccaaag gcagaccgaa ggctccacag  720
gtgtacacca ttccacctcc caaggagcag atggccaagg ataaagtcag tctgacctgc  780
atgataacag acttcttccc tgaagacatt actgtggagt ggcagtggaa tgggcagcca  840
gcggagaact acaagaacac tcagcccatc atggacacag atggctctta cttcgtctac  900
agcaagctca atgtgcagaa gagcaactgg gaggcaggaa atactttcac ctgctctgtg  960
ttacatgagg gcctgcacaa ccaccatact gagaagagcc tctcccactc tcctggtaaa  1020

SEQ ID NO: 34          moltype = AA  length = 326
FEATURE                Location/Qualifiers
REGION                 1..326
                       note = Synthetic Sequence
source                 1..326
                       mol_type = protein
                       organism = synthetic construct
SEQUENCE: 34
MNPSAAVIFC LILLGLSGTQ GQIPLARTVR CNCIHIDDGP VRMRAIGKLE IIPASLSCPR  60
VEIIATMKKN DEQRCLNPES KTIKNLMKAF SQKRSKRAPV PRDCGCKPCI CTVPEVSSVF  120
IFPPKPKDVL TITLTPKVTC VVVDISKDDP EVQFSWFVDD VEVHTAQTQP REEQFNSTFR  180
SVSELPIMHQ DCLNGKEFKC RVNSAAFPAP IEKTISKTKG RPKAPQVYTI PPPKEQMAKD  240
KVSLTCMITD FFPEDITVEW QWNGQPAENY KNTQPIMDTD GSYFVYSKLN VQKSNWEAGN  300
TFTCSVLHEG LHNHHTEKSL SHSPGK                                       326

SEQ ID NO: 35          moltype = DNA  length = 978
FEATURE                Location/Qualifiers
misc_feature           1..978
                       note = Synthetic Sequence
source                 1..978
                       mol_type = other DNA
                       organism = synthetic construct
SEQUENCE: 35
atgaacccaa gtgctgccgt cattttctgc ctcatcctgc tgggtctgag tgggactcaa  60
gggcaaatcc ctctcgcaag gacggtccgc tgcaactgca tccatatcga tgacgggcca  120
gtgagaatga gggccatagg gaagcttgaa atcatccctg cgagcctatc ctgcccacgt  180
gttgagatca ttgccacgat gaaaaagaat gatgagcaga gatgtctgaa tccggaatct  240
aagaccatca agaatttaat gaaagcgttt agccaaaaaa ggtctaaaag ggctcctgtg  300
cccagggatt gtggttgtaa gccttgcata tgtacagtcc cagaagtatc atctgtcttc  360
atcttccccc caaagcccaa ggatgtgctc accattactc tgactcctaa ggtcacgtgt  420
gttgtggtag acatcagcaa ggatgatccc gaggtccagt tcagctggtt tgtagatgat  480
gtggaggtgc acacagctca gacgcaaccc cgggaggagc agttcaacag cactttccgc  540
tcagtcagtg aacttcccat catgcaccag gactgcctca atggcaagga gttcaaatgc  600
agggtcaaca gtgcagcttt ccctgccccc atcgagaaaa ccatctccaa aaccaaaggc  660
agaccgaagg ctccacaggt gtacaccatt ccacctccca aggagcagat ggccaaggat  720
aaagtcagtc tgacctgcat gataacagac ttcttccctg aagacattac tgtggagtgg  780
cagtggaatg ggcagccagc ggagaactac aagaacactc agcccatcat ggacacagat  840
ggctcttact tcgtctacag caagctcaat gtgcagaaga gcaactggga ggcaggaaat  900
actttcacct gctctgtgtt acatgagggc ctgcacaacc accatactga gaagagcctc  960
tcccactctc ctggtaaa                                                978

SEQ ID NO: 36          moltype = AA  length = 326
FEATURE                Location/Qualifiers
REGION                 1..326
                       note = Synthetic Sequence
source                 1..326
                       mol_type = protein
                       organism = synthetic construct
SEQUENCE: 36
```

```
MNPSAAVIFC LILLGLSGTQ GNIPLARTVR CNCIHIDDGP VRMRAIGKLE IIPASLSCPR  60
VEIIATMKKN DEQRCLNPES KTIKNLMKAF SQKRSKRAPV PRDCGCKPCI CTVPEVSSVF  120
IFPPKPKDVL TITLTPKVTC VVVDISKDDP EVQFSWFVDD VEVHTAQTQP REEQFNSTFR  180
SVSELPIMHQ DCLNGKEFKC RVNSAAFPAP IEKTISKTKG RPKAPQVYTI PPPKEQMAKD  240
KVSLTCMITD FFPEDITVEW QWNGQPAENY KNTQPIMDTD GSYFVYSKLN VQKSNWEAGN  300
TFTCSVLHEG LHNHHTEKSL SHSPGK                                      326

SEQ ID NO: 37          moltype = DNA  length = 978
FEATURE                Location/Qualifiers
misc_feature           1..978
                       note = Synthetic Sequence
source                 1..978
                       mol_type = other DNA
                       organism = synthetic construct
SEQUENCE: 37
atgaacccaa gtgctgccgt cattttctgc ctcatcctgc tgggtctgag tgggactcaa  60
gggaatatcc ctctcgcaag gacggtccgc tgcaactgca tccatatcga tgacgggcca  120
gtgagaatga gggccatagg gaagcttgaa atcatccctg cgagcctatc ctgcccacgt  180
gttgagatca ttgccacgat gaaaaagaat gatgagcaga gatgtctgaa tccggaatct  240
aagaccatca agaatttaat gaaagcgttt agccaaaaaa ggtctaaaag ggctcctgtg  300
cccagggatt gtggttgtaa gccttgcata tgtacagtcc cagaagtatc atctgtcttc  360
atcttccccc caaagcccaa ggatgtgctc accattactc tgactcctaa ggtcacgtgt  420
gttgtggtag acatcagcaa ggatgatccc gaggtccagt tcagctggtt tgtagatgat  480
gtggaggtgc acacagctca gacgcaaccc cgggaggagc agttcaacag cactttccgc  540
tcagtcagtg aacttcccat catgcaccag gactgcctca atggcaagga gttcaaatgc  600
agggtcaaca gtgcagcttt ccctgccccc atcgagaaaa ccatctccaa aaccaaaggc  660
agaccgaagg ctccacaggt gtacaccatt ccacctccca aggagcagat ggccaaggat  720
aaagtcagtc tgacctgcat gataacagac ttcttccctg aagacattac tgtggagtgg  780
cagtggaatg ggcagccagc ggagaactac aagaacactc agcccatcat ggacacagat  840
ggctcttact tcgtctacag caagctcaat gtgcagaaga gcaactggga ggcaggaaat  900
actttcacct gctctgtgtt acatgagggc ctgcacaacc accatactga gaagagcctc  960
tcccactctc ctggtaaa                                               978

SEQ ID NO: 38          moltype = AA  length = 340
FEATURE                Location/Qualifiers
REGION                 1..340
                       note = Synthetic Sequence
source                 1..340
                       mol_type = protein
                       organism = synthetic construct
SEQUENCE: 38
MNPSAAVIFC LILLGLSGTQ GIPLARTVRC NCIHIDDGPV RMRAIGKLEI IPASLSCPRV  60
EIIATMKKND EQRCLNPESK TIKNLMKAFS QKRSKRAPGG GGSGGGGSGG GGSVPRDCGC  120
KPCICTVPEV SSVFIFPPKP KDVLTITLTP KVTCVVVDIS KDDPEVQFSW FVDDVEVHTA  180
QTQPREEQFN STFRSVSELP IMHQDCLNGK EFKCRVNSAA FPAPIEKTIS KTKGRPKAPQ  240
VYTIPPPKEQ MAKDKVSLTC MITDFFPEDI TVEWQWNGQP AENYKNTQPI MDTDGSYFVY  300
SKLNVQKSNW EAGNTFTCSV LHEGLHNHHT EKSLSHSPGK                        340

SEQ ID NO: 39          moltype = DNA  length = 1020
FEATURE                Location/Qualifiers
misc_feature           1..1020
                       note = Synthetic Sequence
source                 1..1020
                       mol_type = other DNA
                       organism = synthetic construct
SEQUENCE: 39
atgaacccaa gtgctgccgt cattttctgc ctcatcctgc tgggtctgag tgggactcaa  60
gggatccctc tcgcaaggac ggtccgctgc aactgcatcc atatcgatga cgggccagtg  120
agaatgaggg ccatagggaa gcttgaaatc atccctgcga gcctatcctg cccacgtgtt  180
gagatcattg ccacgatgaa aaagaatgat gagcagagat gtctgaatcc ggaatctaag  240
accatcaaga atttaatgaa agcgtttagc caaaaaaggt ctaaaagggc tcctggcgga  300
ggtggctctg gcggtggcgg atcgggcgga ggtggctctg tgcccaggga ttgtggttgt  360
aagccttgca tatgtacagt cccagaagta tcatctgtct tcatcttccc cccaaagccc  420
aaggatgtgc tcaccattac tctgactcct aaggtcacgt gtgttgtggt agacatcagc  480
aaggatgatc ccgaggtcca gttcagctgg tttgtagatg atgtggaggt gcacacagct  540
cagacgcaac cccgggagga gcagttcaac agcactttcc gctcagtcag tgaacttccc  600
atcatgcacc aggactgcct caatggcaag gagttcaaat gcagggtcaa cagtgcagct  660
ttccctgccc ccatcgagaa aaccatctcc aaaaccaaag gcagaccgaa ggctccacag  720
gtgtacacca ttccacctcc caaggagcag atggccaagg ataaagtcag tctgacctgc  780
atgataacag acttcttccc tgaagacatt actgtggagt ggcagtggaa tgggcagcca  840
gcggagaact acaagaacac tcagcccatc atggacacag atggctctta cttcgtctac  900
agcaagctca atgtgcagaa gagcaactgg gaggcaggaa atactttcac ctgctctgtg  960
ttacatgagg gcctgcacaa ccaccatact gagaagagcc tctcccactc tcctggtaaa  1020

SEQ ID NO: 40          moltype = AA  length = 227
FEATURE                Location/Qualifiers
REGION                 1..227
                       note = Synthetic Sequence
source                 1..227
```

```
                        mol_type = protein
                        organism = synthetic construct
SEQUENCE: 40
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDCLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGK                227

SEQ ID NO: 41           moltype = DNA  length = 681
FEATURE                 Location/Qualifiers
misc_feature            1..681
                        note = Synthetic Sequence
source                  1..681
                        mol_type = other DNA
                        organism = synthetic construct
SEQUENCE: 41
gtgcccaggg attgtggttg taagccttgc atatgtacag tcccagaagt atcatctgtc  60
ttcatcttcc ccccaaagcc caaggatgtg ctcaccatta ctctgactcc taaggtcacg  120
tgtgttgtgg tagacatcag caaggatgat cccgaggtcc agttcagctg gtttgtagat  180
gatgtggagg tgcacacagc tcagacgcaa ccccgggagg agcagttcaa cagcactttc  240
cgctcagtca gtgaacttcc catcatgcac caggactgcc tcaatggcaa ggagttcaaa  300
tgcagggtca acagtgcagc tttccctgcc cccatcgaga aaaccatctc caaaaccaaa  360
ggcagaccga aggctccaca ggtgtacacc attccacctc ccaaggagca gatggccaag  420
gataaagtca gtctgacctg catgataaca gacttcttcc ctgaagacat tactgtggag  480
tggcagtgga atgggcagcc agcggagaac tacaagaaca ctcagcccat catggacaca  540
gatggctctt acttcgtcta cagcaagctc aatgtgcaga agagcaactg ggaggcagga  600
aatactttca cctgctctgt gttacatgag ggcctgcaca accaccatac tgagaagagc  660
ctctcccact ctcctggtaa a                                            681

SEQ ID NO: 42           moltype = DNA  length = 26
FEATURE                 Location/Qualifiers
misc_feature            1..26
                        note = Synthetic Sequence
source                  1..26
                        mol_type = other DNA
                        organism = synthetic construct
SEQUENCE: 42
ctcgaggtgc ccagggattg tggttg                                       26

SEQ ID NO: 43           moltype = DNA  length = 26
FEATURE                 Location/Qualifiers
misc_feature            1..26
                        note = Synthetic Sequence
source                  1..26
                        mol_type = other DNA
                        organism = synthetic construct
SEQUENCE: 43
gggcccttta ccaggagagt gggaga                                       26

SEQ ID NO: 44           moltype =   length =
SEQUENCE: 44
000

SEQ ID NO: 45           moltype =   length =
SEQUENCE: 45
000

SEQ ID NO: 46           moltype =   length =
SEQUENCE: 46
000

SEQ ID NO: 47           moltype = DNA  length = 30
FEATURE                 Location/Qualifiers
misc_feature            1..30
                        note = Synthetic Sequence
source                  1..30
                        mol_type = other DNA
                        organism = synthetic construct
SEQUENCE: 47
ctcgagagga gcccttttag accttttttg                                   30

SEQ ID NO: 48           moltype = AA  length = 98
FEATURE                 Location/Qualifiers
source                  1..98
                        mol_type = protein
                        organism = Homo sapiens
SEQUENCE: 48
MNQTAILICC LIFLTLSGIQ GVPLSRTVRC TCISISNQPV NPRSLEKLEI IPASQFCPRV  60
EIIATMKKKG EKRCLNPESK AIKNLLKAVS KERSKRSP                          98
```

-continued

```
SEQ ID NO: 49          moltype = AA  length = 98
FEATURE                Location/Qualifiers
source                 1..98
                       mol_type = protein
                       organism = Mus musculus
SEQUENCE: 49
MNPSAAVIFC LILLGLSGTQ GIPLARTVRC NCIHIDDGPV RMRAIGKLEI IPASLSCPRV  60
EIIATMKKND EQRCLNPESK TIKNLMKAFS QKRSKRAP                          98
```